(12) United States Patent
Papaioannou et al.

(10) Patent No.: US 7,517,913 B2
(45) Date of Patent: Apr. 14, 2009

(54) POLYAMINE CONJUGATES WITH ACIDIC RETINOIDS AND PREPARATION THEREOF

(76) Inventors: Dionysios Papaioannou, University of Patras Department of Chemistry, Patras (GR) 26504; Dionysios Drainas, University of Patras, School of Medicine, Department of Biochemistry, Patras (GR) 26504; Dionysios Tsambaos, University of Patras, Department of Dermatology, School of Medicine, Patras (GR) 26504

( * ) Notice: Subject to any disclaimer, the term of this patent is extended or adjusted under 35 U.S.C. 154(b) by 0 days.

(21) Appl. No.: 10/549,905

(22) PCT Filed: Aug. 22, 2002
(Under 37 CFR 1.47)

(86) PCT No.: PCT/GR02/00045

§ 371 (c)(1),
(2), (4) Date: Sep. 20, 2005

(87) PCT Pub. No.: WO2004/018001

PCT Pub. Date: Mar. 4, 2004

(65) Prior Publication Data

US 2006/0189696 A1    Aug. 24, 2006

(51) Int. Cl.
C07D 233/00    (2006.01)
C07D 235/00    (2006.01)
C07D 237/00    (2006.01)
C07D 239/00    (2006.01)
A01N 37/18    (2006.01)
A61K 31/16    (2006.01)

(52) U.S. Cl. .................................. 514/613; 564/123
(58) Field of Classification Search .................. None
See application file for complete search history.

(56) References Cited

U.S. PATENT DOCUMENTS 6,344,206 B1    2/2002    Nguyen et al.

FOREIGN PATENT DOCUMENTS

WO    WO98/34646    8/1998
WO    2004/018001 A1    3/2004

OTHER PUBLICATIONS

Manfredini et al. Retinoic Acid Conjugates as Potential Antitumor Agents: Synthesis and Biological Activity of Conjugates with Ara-A, Ara-C, 3(2H)-Furanone, and Aniline Mustard Moieties. Journal of Medicinal Chemistry, 1997, 40, 3851-3857.*

(Continued)

Primary Examiner—James O Wilson
Assistant Examiner—Noble Jarrell
(74) Attorney, Agent, or Firm—Stanislaus Aksman; Roberts Mlotkowski Safran & Cole P.C.

(57) ABSTRACT

Invented are novel polyamine conjugates which have been readily obtained using as key-step the condensation of linear, conformationally restricted, cyclic and branched polyamines or suitably protected derivatives with vitamin A derivatives. These compounds inhibit the ribozyme ribonuclease P (RNase P) and the production of interleukin-2 (IL-2) and interferon-γ (INF-γ) by peripheral blood mononuclear cells in vitro.

9 Claims, 12 Drawing Sheets

OTHER PUBLICATIONS

Giuseppe et al. Expert Opinion on Therapeutic Patents, 1997, 7(4), 307-323.*

"Amines", http://users.ox.ac.uk/~mwalter/web_05/year1/organinitrogen/amines.html, accessed Sep. 7, 2007.*

G. Karigiannis and D. Papaioannou, ' Structure, Biological Activity and Synthesis of Polyamine Analogues and Conjugates, European Journal of Organic Chemistry, 1841-1843 (2000).

V. Kuksa, R. Buchay and P. Kong Thoo Liu; Synthesis of Polyaanines Their Derivatives, Analogues and Conjugates, Synthesis, 1189-1207 (2000).

The Retinoids: Biology, Chemistry and Medicine 2nd Ed., M.B. Sporu, A.B. Roberts and D.S. Goodman, Eds. Raven Press, New York, 1994 pp. 136-142.

S. Manfredini , D: Simoni, R. Ferroni, R. Bazzanini, S. Vertuani, S. Hatse, T. Balzarini and G. De Clerca, 1 Retinoic Acid Conjuge-tes with Ara-C, 3(2H)-Furanone, and Aniline Mustard Moieties; Journal of Medicinal Chemistry, 40, 3851-3857 (1997).

M. Mitsopoulou, N. Tsiakopoulos, G. Chochos, G. Magoulas and D. Papaioaunou, Simple Syntheses of Cyclic Polyamines using Selectively N-Tritylated Polymines ans Succinic Anhydride; Tetrahedron Letters, 43,2593-2596 (2002).

Papadimou, S. Georgiou, D. Tsauboas and D. Drainas, 'Inhibition of Ribounuclease P Activity by Retinoids', The J. Biological Chemistry, 273 (38), 24375-24378(1998).

Blagbrough, I.S. et al, Polyamines and polyamine amides as potent selective receptor probes, novel therapeutic lead compounds and synthetic vectors in gene therapy, Pharmaceutical Sciences, 1997, pp. 223-233, vol. 3 Issue 5-6, School of Pharmacy and Pharmacology, University of Bath, United Kingdom. Abstract.

Schulz, Stefan, The Chemistry of Spider Toxins and Spider Silk, Angew. Chem. Int., 1997, pp. 314-326, vol. 36, Institute fuer Organische Chemie der Universitaet, Hamburg, Germany.

Karigiannis, George et al, Structure, Biological Activity and Synthesis of Polyamine Analogues and Conjugates, Journal of Organic Chemistry, 2000, pp. 1841-1863, University of Patras, Patras, Greece.

Manfredini, Stefano et al, Retinoic Acid Conjugates as Potential Antitumor Agents: Synthesis and Biological Activity of Conjugates with Ara-A, Ara-C, 3(2H)-Furanone, and Aniline Mustard Moieties, Journal of Medicinal Chemistry, 1997, pp. 3851-3857, vol. 40, American Chemical Society.

Militsopoulou, Maria et al., Simple syntheses of cyclic polyamines using selectively N-tritylated polyamines and succinic anhydride, Tetrahedron Letters, 2002, pp. 2593-2596, vol. 43, Elsevier Science Ltd.

Vassis, Stratos et al., Simple synthesis of the polymine alkaloid tenuilobine and analogues using selectively N-tritylated polyamines and dicarboxylic acids as bridging elements, Tetrahedron Letters, 2002, pp. 2597-2600, vol. 43, Elsevier Science Ltd.

Vassis, Stratos et al., Simple syntheses of N-alkylated spermidine fragments and analogues of the spermine alkaloid kukoamine A, Tetrahedron Letters, 2001, pp. 1579-1582, vol. 42, Elsevier Science Ltd.

Karigiannis, George et al., Simple fragment synthesis of all four isomers of the spermine alkaloid kukoamine, Tetrahedron Letters, 1998, pp. 5117-5120, vol. 39, Elsevier Science Ltd.e.

O'Sullivan, Mary et al., A one-step Procedure for the selective trifluoroacetylation of primary amino groups of polyamines, Tetrahedron Letters, 1995, pp. 3451-3452, vol. 36, No. 20, Elsevier Science Ltd.

Mamos, Petros et al., Simple total syntheses of N-substituted Polyamine Derivatives using N-tritylamino acids, Tetrahedron Letters, 1995, pp. 5187-5190, vol. 36, No. 29, Elsevier Science Ltd.

Papadimou, Evangelia et al., Inhibitory effects of arotinoids on tRNA biogenesis, Skin Pharmacology and Applied Skin Physiology, 2000, pp. 345-351, vol. 13, S. Karger AG.

Papadimou, Evangelia et al., Inhibition of Ribonuclease P activity by retinoids, The Journal of Biological Chemistry, 1998, pp. 24375-24378, vol. 273, No. 38, The American Society for Biochemistry and Molecular Biology, Inc.

Pavlidou, Despina et al., Isolation of ribonuclease P activity from human epidermis and its regulation by retinoids in vitro, Acta Derm Venereol, 2006, pp. 114-118, vol. 86, Acta Dermato-Venereologica, Greece.

Papadimou, Evangelia et al., Retinoids inhibit human epidermal keratinocyte RNase P activity, The Journal of Biological Chemistry, 2003, pp. 457-462, vol. 384, Walter de Gruyter, New York.

Xu, Daqiang et al., Ethyl trifluoroacetate: A powerful reagent for differentiating amino groups, Tetrahedron Letters, 1995, pp. 7357-7360, vol. 36, No. 41, Elsevier Science Ltd., Great Britain.

Blagbrough, Ian et al., Cheno-, Urso-, and deoxycholic acid spermine conjugates: Relative binding affinities for calf thymus DNA, Tetrahedron Letters, 2000, pp. 3439-3447, vol. 56, Elsevier Science Ltd.

Krakowiak, Krzysztof et al., Selective protection of the primary amine functions of linear tetraamines using the trityl group, Synthetic Communications, 1998, pp. 3451-3459, vol. 28(18), Marcel Dekker, Inc.

De Luga, Luigi, Retinoids and their receptors in differentiation, embryogenesis, and neoplasia, The Faseb Journal, 1991, pp. 2924-2933, vol. 5, National Cancer Institute, USA.

Lotan, R. et al., Nuclear receptors for retinoids: mediators of retinoid effects on normal and malignant cells, Biomed & Pharmacother, 1991, pp. 145-156, vol. 45, Elsevier Paris, USA.

Leid, Mark et al., Multiplicity generates diversity in the retinoic acid signalling pathways, TIBS- Oct. 17, 1992, pp. 427-433, vol. 17, Elsevier Science Publishers, UK.

Giguere, Vincent et al., Identification of a receptor for the morphogen retinoic acid, Nature, vol. 330, Dec. 17, 1987, pp. 624-629, Nature Publishing Group.

Petkovich, Martin et al., A human retinoic acid receptor which belongs to the family of nuclear receptors, Nature, vol. 330, Dec. 3, 1987, pp. 444-450, Nature Publishing Group.

Lippman, Scott M. et al., Advances in the Development of Retinoids as Chemopreventive Agents, Symposium: Diet, Natural Products and Cancer Prevention: Progress and Promise, Presented Apr. 17-21, 1999, Washington, DC, The Journal of Nutrition Supplement, pp. 479S-482S, 2000; American Society for Nutritional Sciences.

Papadimou, Evangelia et al., Modulation of ribonuclease P activity by calcipotriol, Eur. J. Biochem., vol. 267, pp. 1173-1177, (2000), FEBS.

Drainas, D. et al., Dose-Dependent Inhibition of Ribonuclease P Activity by Anthralin, Skin Pharmacology and Applied Skin Physiology, 2000, vol. 13, pp. 128-132, S. Karger AG, Basel.

Papadimou, Evangelia et al., Additive Inhibitory Effect of Calcipotriol and Anthralin on Ribonuclease P Activity, Biochemical Pharmacology, vol. 60, pp. 91-94, 2000, Elsevier Science Inc.

Stathopoulos, Constantinos et al., Partial purification and characterization of RNase P from Dictyostelium discoideum, Eur. J. Biochem., vol. 228, pp. 976-980, (1995), FEBS.

Frank, Daniel N. et al., Ribonuclease P: Unity and Diversity in a tRNA Processing Ribozyme, Annual Review of Biochemistry, 1998, vol. 67, pp. 153-180, Annual Reviews.

Manfredini, Stefano et al., Retinoic Acid Conjugates as Potential Antitumor Agents: Synthesis and Biological Activity of Conjugates with Ara-A, Ara-C, 3(2H)-Furanone, and Aniline Mustard Moieties, Journal of Medicinal Chemistry, 1997, vol. 40, No. 23, pp. 3851-3857, American Chemical Society.

Astrom, Anders et al., Retinoic Acid and Synthetic Analogs Differentially Activate Retinoic Acid Receptor Dependent Transcription, Biochemical and Biophysical Research Communications, vol. 173, No. 1, 1990, pp. 339-345, Academic Press, Inc.

Michel, Serge et al., Determination of Retinoid Activity by Enzyme-Linked Immunosorbent Assay, Analytical Biochemistry, vol. 192, pp. 232-236, (1991), Academic Press, Inc.

Elder, James T. et al ., Retinoid Induction of CRABP II mRNA in Human Dermal Fibroblasts: Use as a Retinoid Bioassay, The Journal of Investigative Dermatology, vol. 106, No. 3, Mar. 1996, pp. 517-521, The Society for Investigative Dermatology, Inc.

Kuksa, Vladimir et al., Synthesis of Polyamines, Their Derivatives, Analogues and Conjugates, Synthesis 2000, No. 9, 1189-1207 (full copy of the reference).

Blagbrough, Ian S. et al., Polyamines and Polyamine Amides as Potent Selective Receptor Probes, Novel Therapeutic Lead Compounds and Synthetic Vectors in Gene Therapy, Pharmaceutical Sciences, 1997, 3; 223-233 (full copy of the reference).

Tsambaos, Dionysios, Retinoide: Ein neues Kapitel der Dermotherapie, Dermatosen in Beruf und Umwelt: Occupation and Environment, vol. 44, No. 4, (1996), pp. 149, 182-183. (English Abstract).

* cited by examiner $R^1$

5

$R^2$

6

$R^5$

7

$R^6$

8

$R^3$

9

$R^4$

10

POLYAMINE CONJUGATES WITH ACIDIC RETINOIDS AND PREPARATION THEREOF

FIELD OF THE INVENTION

This invention relates to the preparation of a series of novel polyamine conjugates with vitamin A derivatives which inhibit the ribozyme RNase P and the production of IL-2 and IFN-γ by peripheral blood mononuclear cells in vitro and have potential therapeutic applications in neoplastic, keratinization and inflammatory disorders. In particular, the invention relates to conjugates, obtained from the condensation of linear, conformationally restricted, cyclic and branched polyamines with acidic retinoids, such as all-trans-retinoic acid.

BACKGROUND OF THE INVENTION

Linear polyamines, like spermine (SPM, 1) and spermidine (SPD, 2), and their compounds with other natural products, collectively coined as polyamine conjugates, are widely distributed in living organisms and exhibit interesting biological properties.

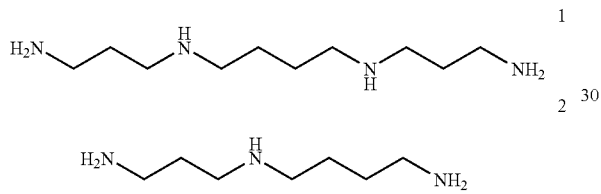

In order to determine structure-biological activity relationships and possibly identify lead compounds for the development of polyamine-based pharmaceuticals, a variety of linear, branched, conformationally restricted and cyclic polyamine analogues and conjugates have been synthesized (Blagbrough et al., PHARM. SCI., 3, 223 (1997); Schulz et al., ANGEW. CHEM. INT. END. ENGL., 36, 314 (1997); Papaioannou et al., EUR. J. ORG. CHEM., 1841 (2000) and Kong Thoo Lin et al., SYNTHESIS, 1189 (2000)). Due to their polycationic nature, polyamines interact strongly with nucleic acids and play an important role in their biosynthesis and metabolism. They stabilize DNA conformation and can induce conformation changes through the formation of intra- or intermolecular bridges. Polyamines cause specific modifications of specialized RNA molecules, stabilize ribonucleases and stimulate the action of ribonucleases and ribozymes. They exert pleiotropic effects on protein synthesis, are essential for normal growth and involved in the differentiation processes of mammalian cells. The concentrations of polyamines and the enzymes responsible for their biosynthesis are notably higher in rapidly proliferating mammalian cells; generally, these concentrations increase in all cells upon induction of differentiation. Polyamines are directly responsible for the increased rate of the macromolecular synthesis occurring during tumour development and growth. Inhibition of the biosynthetic enzymes producing polyamines and of the polyamine uptake system responsible for feeding the cell with exogenous polyamines have emerged as very attractive targets for cancer chemotherapy. Recently, selectively N-alkylated polyamines which partially mimic natural polyamine behaviour, inhibit cell growth and are metabolically stable have been developed as novel anticancer agents (for leading references see the review by Papaioannou et al., EUR. J. ORG. CHEM., 1841 (2000)).

The retinoids constitute a large family of organic compounds structurally related to the naturally occurring Vitamin A (retinol, 3) and analogues, such as retinal (4) and all-trans-retinoic acid (5) and a variety of other synthetic analogues, such as acitretin (6), 13-cis-retinoic acid (7) and 9-cis-retinoic acid (8). The polyene chain-shortened all-trans-retinoic acid analogues 9 and 10 may be also considered as members of this family.

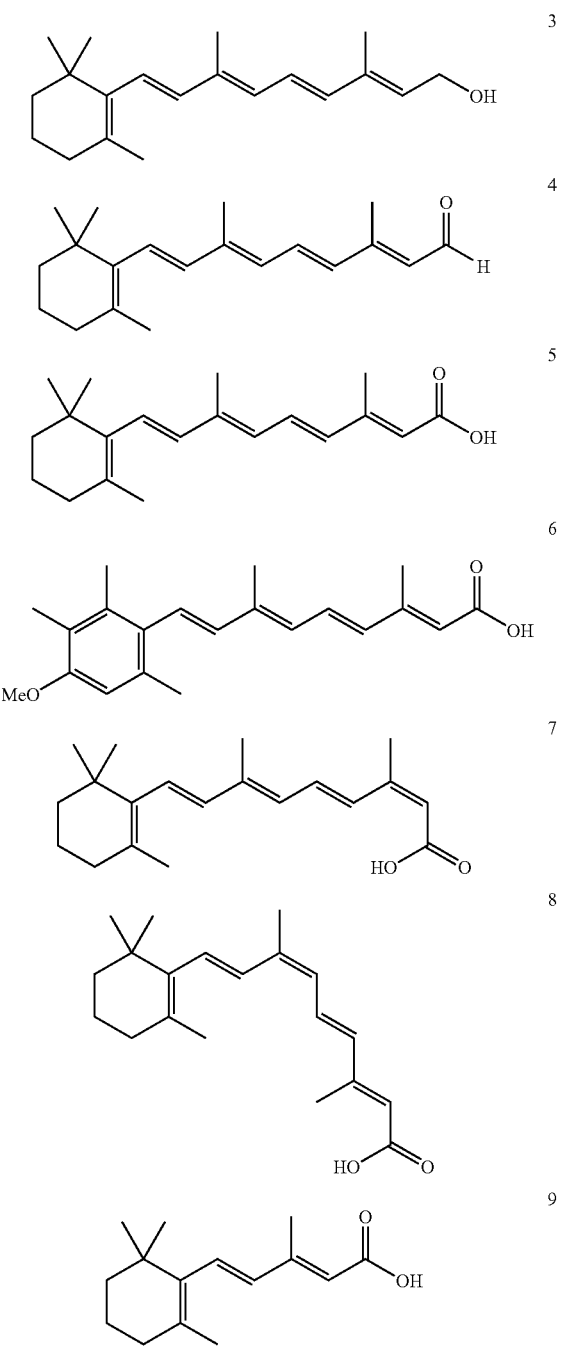

-continued

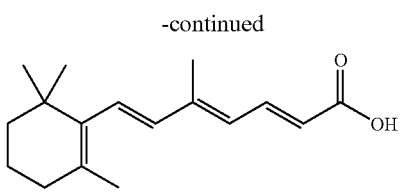

10

Retinoids can cause specific biological responses upon binding to and activating special receptors or groups of receptors. Natural and synthetic retinoids play an important role in vision, cell growth, reproduction, proliferation and differentiation of various epithelial or non-epithelial tissues. Although they are already widely used in systemic and topical treatment of various disorders, retinoids reveal a considerable number of side-effects even when used in therapeutic doses. Thus, numerous new retinoid analogues have been synthesized in an attempt to improve the therapeutic index, biological profile and selectivity of these compounds for clinical application in dermatology, oncology, rheumatology and immunology (for general monographies see Sporn, Roberts and Goodman (Eds.), The Retinoids, vol. 1 and 2, Academic Press, Orlando, 1984; Sporn and Roberts, CIBA FOUND. SYMP., 113, 1 (1985); Sporn, Roberts and Goodman (Eds.), The Retinoids: Biology, Chemistry and Medicine, $2^{nd}$ ed., Raven Press, New York, 1994; Dawson and Okimura (Eds.), Chemistry and Biology of Synthetic Retinoids, CRC Press, Boca Raton, 1990; Packer (Ed.), Methods in Enzymology, Academic Press, vol. 189, part A, 1990 and vol. 190, part B, 1991)). The clinical application of synthetic retinoids in the management of recalcitrant and previously incurable neoplastic, inflammatory and keratinization disorders has introduced a real revolution in dermatology and other medical fields (Tsambaos, DERMATOSEN, 44, 182 (1996), Muindi, CANCER TREAT. RES., 87, 305 (1996)). By regulating gene expression, retinoids are capable of regulating the differentiation and growth of transformed cells or of inhibiting the malignant transformation of a variety of cells reversing their differentiation (DeLuca, FASEB J., 5, 2924 (1991), Lotan and Glifford, BIOMED. PARMACOTHER., 45, 145 (1991)). In the mechanisms of regulation of gene expression by retinoids certain members of the large family of steroid and thyroid gland hormones receptors are involved, that is nuclear proteins to which retinoids specifically bind (DeLuca, FASEB J., 5, 2924 (1991), Leid et al., TRENDS BIOCHEM. SCI., 17, 427 (1992)). Retinoid receptors have been already isolated and studied (Redfern, PATHOBIOL. 60, 254 (1992), Giguere et al., NATURE, 330, 624 (1987), Petkovich et al., NATURE, 330, 444 (1987)). They act as transcription factors following activation by suitable ligands. Currently, the development of new retinoid-based drugs is based on the synthesis of novel ligands for the retinoic acid receptors RARα,β,γ and RXRα,β,γ and the orphan receptors (Lippman and Lotan, J. NUTR. 130(2S Suppl), 479S (2000)).

It has been recently reported that natural retinoids, like retinoic acid and retinol, as well as synthetic analogues of retinoic acid, e.g. isotretinoin (13-cis-retinoic acid), acitretin and the arotinoids Ro 13-7410, Ro 15-0778, Ro 15-1570 and Ro 13-6298 but also other compounds, e.g. calcipotriol, anthralin and their combination, known for their antipsoriatic activity, inhibit the enzyme ribonuclease P (RNase P) (Papadimou et al., J. BIOL. CHEM. 273, 24375 (1998), Papadimou et al., SKIN PHARMACOL. APPL. SKIN PHYSIOL. 13, 345 (2000), Papadimou et al., EUR. J. BIOCHEM. 267, 1173 (2000), Drainas et al., SKIN PHARMACOL. APPL. SKIN PHYSIOL.13, 128 (2000), Papadimou et al., BIOCHEM. PHARMACOL. 60, 91 (2000)), which has been isolated and characterized from the slime mold *Dictyostelium discoideum* (Stathopoulos et al.; EUR.J. BIOCHEM. 228, 976 (1995)) and from normal human epidermal keratinocytes.(Drainas et al, unpublished results). These finding advocate the hypothesis that retinoids, in addition to regulating DNA transcription, can also regulate the activity of enzymes playing key-roles in macromolecular biosynthesis, by their implication in post-transcriptional processes, in which binding to the retinoic acid receptors is not involved. RNase P is responsible for the ripening of the 5' terminus of precursor tRNA molecules. RNase P activity have been found in all pro- and eucaryotic organisms studied so far (Frank and Pace ANNU. REV. BIOCHEM. 67, 153 (1998)). RNase P enzymes are complexes of RNA with proteins and their activity is mainly attributed to their RNA subunit. Several findings indicate that the structure of the RNA subunit is of similar size in pro- and eucaryotic organisms and that the structures of RNase P from different eucaryotic organisms are similar. For these reasons, it appears that RNase P from *D. discoideum* and human epidermal keratinocytes are good models for the identification and development of new inhibitors.

SYNOPSIS OF INVENTION

Attaching a polyamine on another bioorganic molecule results in the formation of a polyamine conjugate. Depending on the structure of the non-polyamine moiety, these conjugates are designed to exhibit improved biological activity on particular cellular targets or combine the activities of the constituent molecules. The compounds (conjugates) of the present invention were synthesized in an attempt to combine the biological profiles of polyamines and retinoids. They were all obtained by using as key-step the coupling of the polyamine analogues tabulated in FIG. 1 with the retinoids depicted in FIG. 2. It was anticipated that the polyamine affinity for nucleic acids, e.g. the RNA part of RNase P, would enforce the binding of natural and synthetic retinoids on the same molecule. Recently, $N^1$, $N^3$-diretinoyl-1,3-diaminopropane was synthesized, from 1,3-diaminopropane and retinoyl chloride, as potential antitumour agent but showed low cytostatic activity (Manfredini et al., J. MED. CHEM., 40, 3851 (1997)), whereas cosmetic and/or dermatological compositions consisted of retinol or retinol esters and polyamine polymers were prepared and showed that the polyamine polymers provide superior stabilization to retinol in skin care compositions compared to known products with antioxidant or retinol stabilizing properties (Nguyen et al, U.S. Pat. No. 6,344,206 B1).

Indeed, the conjugates described in the present invention reveal stronger inhibitory effects on RNase P isolated from *D. discoideum* and human epidermal keratinocytes than the parent retinoids or a combination of free polyamines and the corresponding retinoids (Table 1). From the same studies it appears that the more free amino functions in the conjugates are available to interact, the stronger is the RNase P inhibition (e.g. the spermine conjugate with all-trans-retinoic acid is a stronger inhibitor than the corresponding spermidine conjugate). On the other hand, conjugates with two retinoid residues are more active than those with one residue (e.g. spermine bearing two all-trans-retinoic acid residues is a stronger inhibitor than spermine bearing only one). In addition, these compounds show an inhibitory effect on the production of IL-2 and IFN-γ by peripheral blood mononuclear cells of healthy human subjects in vitro. In sharp contrast, the currently available retinoids show a stimulatory effect on the production of these cytokines. These results indicate that the compounds described herein have significant potential for clinical application in the treatment of neoplastic, inflammatory and keratinization disorders.

SUMMARY OF THE INVENTION AND DESCRIPTION OF THE PREFERRED EMBODIMENTS

Figure 1:
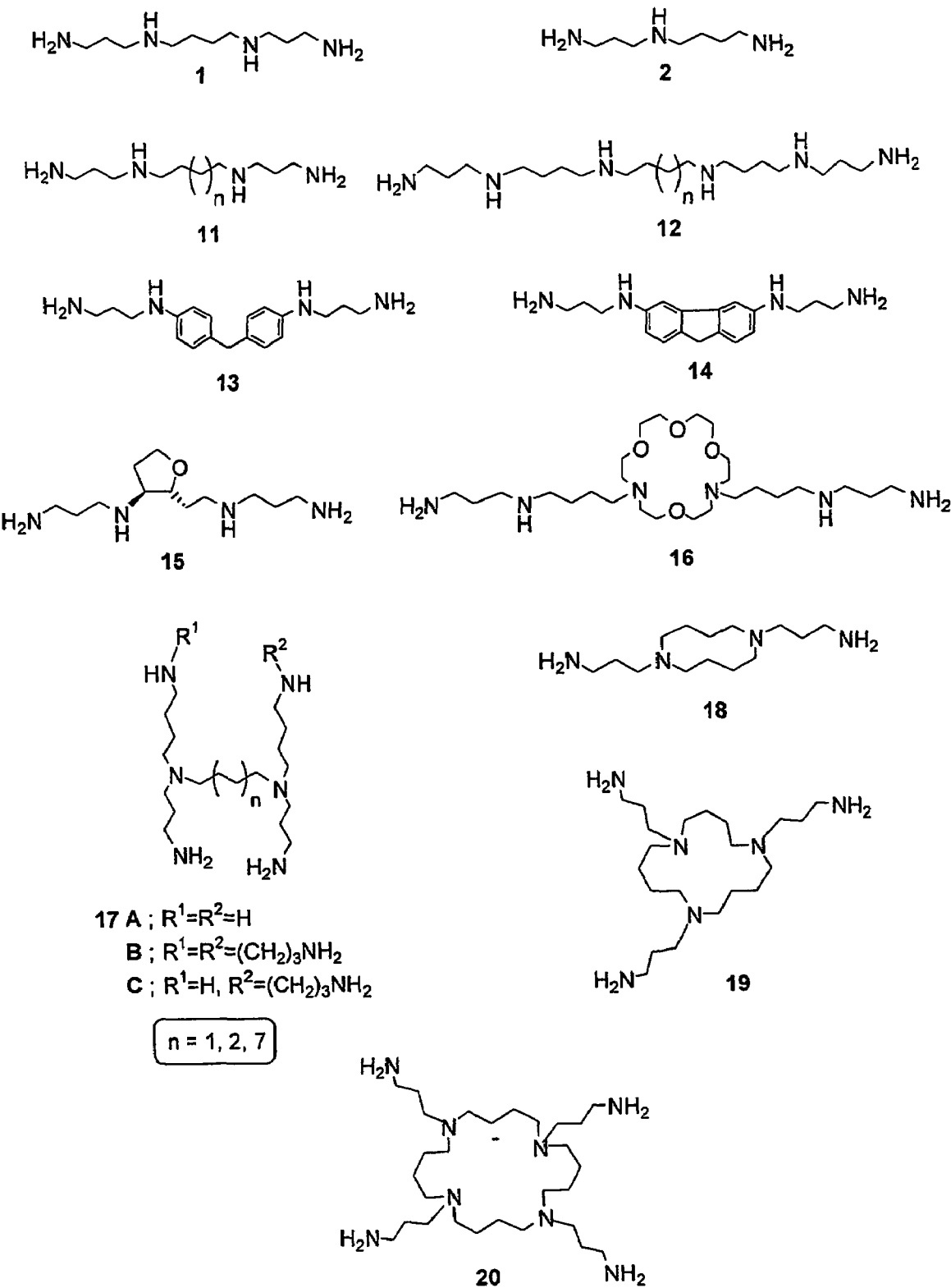
FIG. 1: Structures of polyamines used to prepare the conjugates described in the present invention
Figure 2:
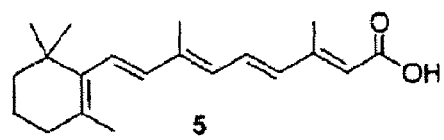
FIG. 2: Structures of retinoids used to prepare the conjugates described in the present invention
Figure 2:
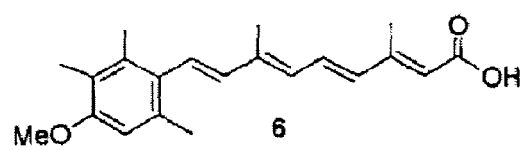
Figure 2:
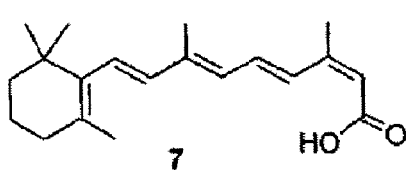
Figure 2:
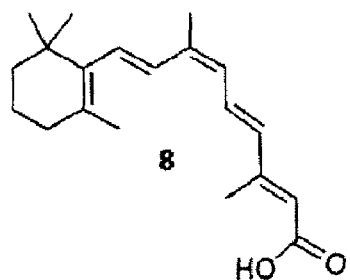
Figure 2:
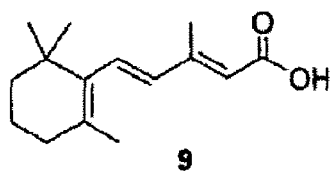
Figure 2:
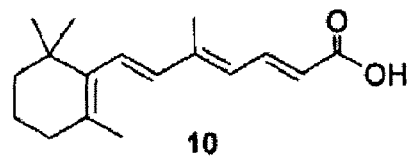

The compounds of the present invention are polyamine conjugates with acidic retinoids, which are prepared through the condensation of either free polyamines or selectively protected polyamines, from those depicted in FIG. 1, with either the retinoids directly or the corresponding succinimidyl esters of the acidic retinoids tabulated in FIG. 2. The conjugates of the present invention are inhibitors of the enzyme RNase P, isolated from the slime mold *D. discoideum* and human epidermal keratinocytes. The most potent inhibitor among these conjugates has also shown excellent inhibitory effects on the production of IL-2 and INF-γ by peripheral blood mononuclear cells. Thus, it is reasonable to assume that these compounds may be useful in the management of inflammatory disorders.

The biological evaluation of the conjugates of the present invention through the examination of their inhibitory activity on RNase P from slime mold *D. discoideum* and human epidermal keratinocytes constitutes a rapid and safe test for evaluation of their potential to modulate the epithelial differentiation and proliferation and to reverse the malignant transformation of epithelial cells. Thus, alternative laborious tests for retinoid screening based on the retinoic acid receptor (RAR) mediated transcriptional activation (Astrom, BIOCHEM. BIOPHYS. RES. COMMUN., 173, 339 (1990)), or suppression of the expression of an enzyme (Michel, ANAL. BIOCHEM., 192, 232 (1991)), or the induction of a protein RNA (Elder, J. IVEST. DERMATOL. 106, 517 (1996)) become unnecessary.

One subfamily of the compounds of the present invention is represented by the following general formulae 3DI-3DIX, which represent conjugates of linear polyamines, of variable numbers of carbon and nitrogen atoms in the chain, with acidic retinoids.

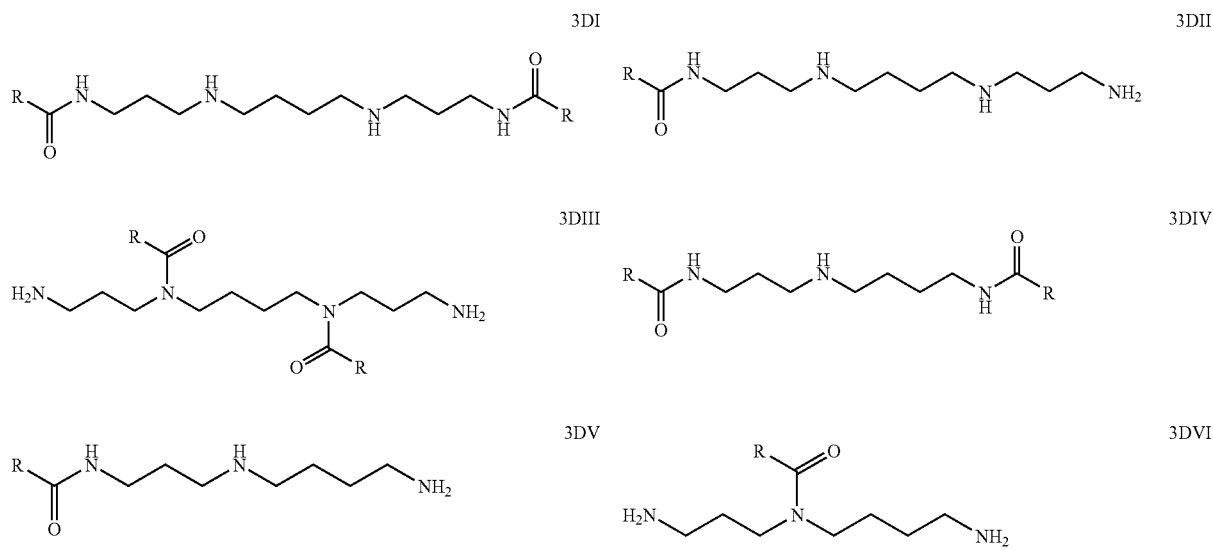

3DVII

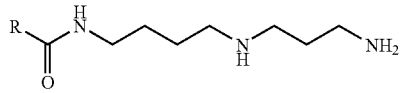

3DVIII

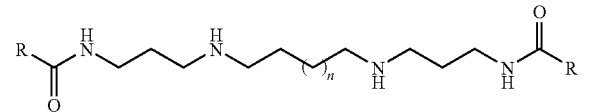

3DIX

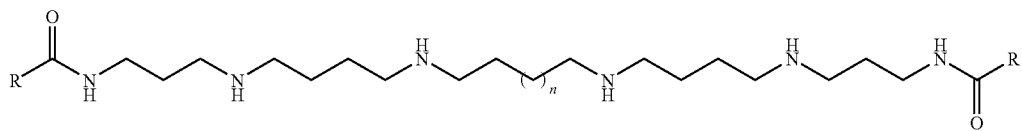

a: R = R¹
b: R = R²
c: R = R³
d: R = R⁴
e: R = R⁵
f: R = R⁶

The subscript n in the formula 3DVIII varies from 2-9 and in the formula 3DIX from 1-9. The substituent R is one of the following substituents $R^1$-$R^6$, preferably $R^1$.

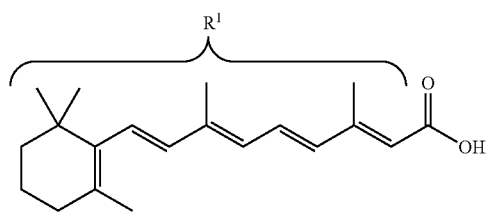

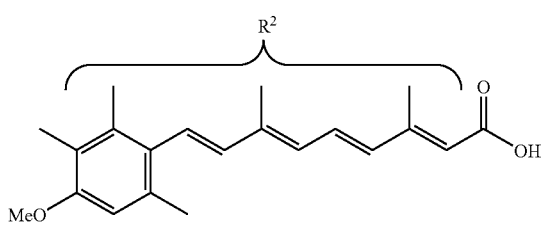

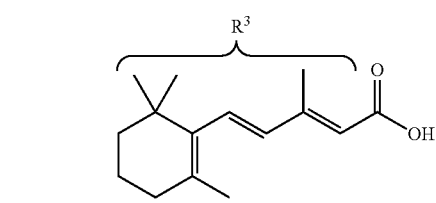

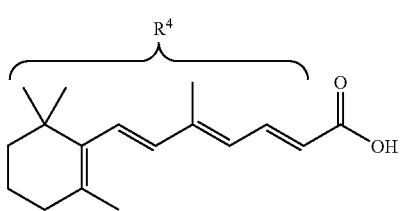

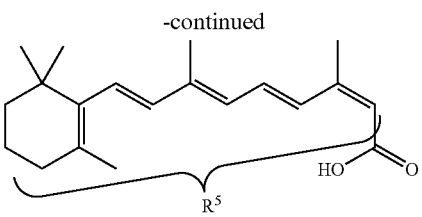

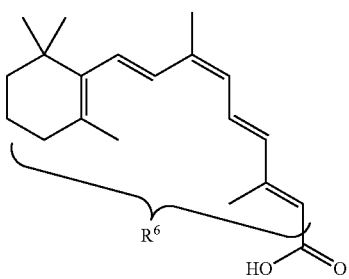

The other subfamily of the compounds of the present invention with the general formulae 3DX-3DXVII, includes conjugates of conformationally restricted, cyclic and branched (dimeric) polyamines with acidic retinoids. Restriction of conformation in the polyamine moiety is imposed by e.g. aromatic rings incorporated in the chain (conjugates 3DX and 3DXI) or heterocyclic rings (conjugates 3DXII) whereas the cyclic polyamines used are of various ring-sizes and contain different numbers of carbon, nitrogen and oxygen atoms in the ring (conjugates 3DXIII-3DXVI). In this subfamily, the polyamine moiety also consists of symmetric or asymmetric polyamine (spermine and spermidine) dimers (conjugates 3DXVII). In this category of compounds, the substituent R is one of the above mentioned, $R^1$-$R^6$ preferably $R^1$, whereas n is one of the numbers 1, 2 and 7. In compounds 3DXVIIA, R' is identical to R" and equal to COR. In compounds 3DXVIIB, R' is also identical to R" but equal to $(CH_2)_3NHCOR$. Finally, in compounds 3DXVIIC, R' is equal to COR and R" is equal to $(CH_2)_3NHCOR$.

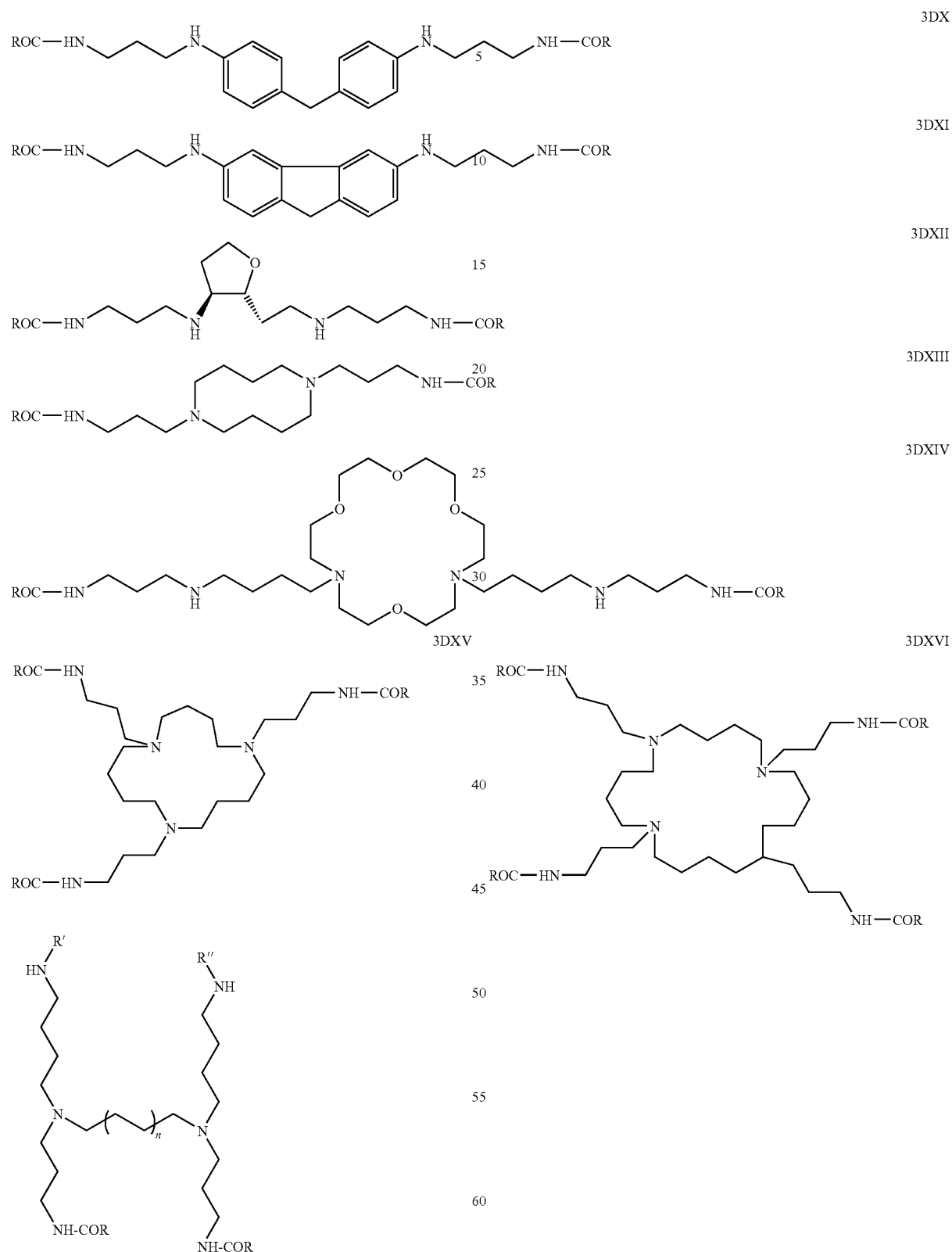

Synthesis

Figure 3:
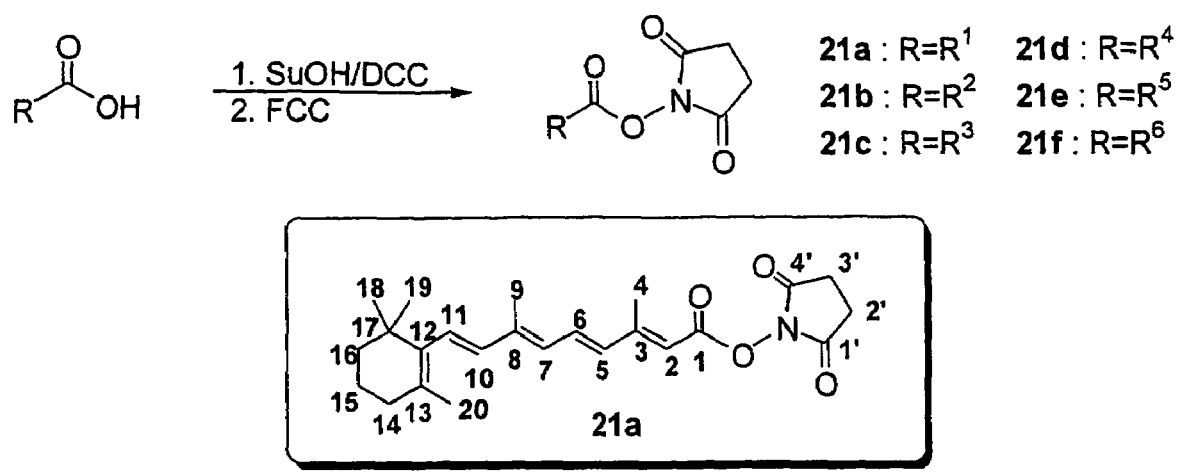
FIG. 3: General method for the preparation of isolable succinimidyl esters of acidic retinoids

Key-reaction in the synthesis of the polyamine amides described in the present invention is the coupling of an acidic retinoid or activated derivatives of an acidic retinoid with either a free polyamine (direct method) or a suitably protected derivative of a polyamine (indirect method). The acidic retinoids used in this work were either commercially available, e.g. all-trans-retinoic acid (ALDRICH), 9- and 13-cis-retinoic acid (SIGMA) and acitretin (ROCHE) or synthesized using standard reactions, e.g. the polyene chain-shortened all-trans-retinoic acid analogues 9 and 10 depicted in FIG. 2. In particular, β-ionylideneacetic acid (9) was obtained according to a published protocol (Tietze und Eicher, 'Reactionen und Synthesen im organisch-chemischen Praktikum', Thieme, New York, 1981, p 445), whereas β-ionylidene-trans-crotonic acid (10) was synthesized from β-ionylidenethanol (previous reference, p. 446) through a three-steps protocol involving oxidation to the corresponding aldehyde with o-iodoxybenzoic acid (IBX) in DMSO (Frigerio et al, J. ORG. CHEM., 60, 7272 (1995)), Wittig reaction with diethyl (ethoxycarbonyl)methylphosphonate and finally saponification. Taking into consideration the sensitivity of retinoids towards strongly acidic reagents, we chose to activate the acidic retinoids in the form of their corresponding 'active' esters with N-hydroxysuccinimide (HOSu) which are hydrolytically relatively stable and can be readily purified, if necessary, with flash column chromatography (FCC). In addition, the succinimidyl esters of α,β-unsaturated carboxylic acids react only with the primary amino group of polyamines (Papaioannou et al, TETRAHEDRON LETT., 43, 2593 (2002)). The succinimidyl esters of acidic retinoids (21) are simply obtained (FIG. 3) by treating the acidic retinoid with HOSu in the presence of the coupling agent N,N'-dicyclohexylcarbodiimide (DCC) (see EXAMPLE 1). The succinimidyl esters 21 thus obtained are of sufficient purity to be used in the next step. However, pure samples can be readily obtained through purification with FCC. Esters 21 are then used to acylate the primary amino groups of either the free polyamines (direct method) or polyamines protected at their secondary amino functions with protecting groups, such as 9-fluorenylmethoxycarbonyl (Fmoc) or trifluoroacetyl (Tfa), which can be subsequently removed under basic conditions (indirect method). Examples of both methodologies in the preparation of linear $N^{\omega}$-mono (3DII)- and $N^{\alpha}$,$N^{\omega}$-diacetylated tetra-amines (3DI and 3DVIII) and $N^{\alpha}$,$N^{\omega}$-diacetylated triamines (3DIV) and hexa-amines (3DIX) are presented in FIG. 4 and detailed under the EXAMPLES 2 and 3. Useful precursors for the indirect methodology are polyamines bearing the triphenylmethyl (trityl, Trt) protecting group at their terminal amino functions, like 22, 26 and 27, whose preparation has been described by one of the inventors using the amide approach for the assembly of the polyamine chain (Papaioannou et al, TETRAHEDRON LETT., 36, 5187 (1995); 39, 5117 (1998); 42, 1579 (2001); 43, 2593 and 2597 (2002) and Papaioannou et al, in 'Drug Discovery and Design: Medical Aspects', J. Matsoulkas and T. Mavromoustakos (Eds.), IOS Press, Amsterdam, 2002, in press). These precursors are then routinely protected at their secondary amino function(s) with e.g. the Fmoc group and finally detritylated by a solution of trifluoroacetic acid (TFA) in dichloromethane (DCM). Mono- and/or bisacylation is then performed using one or two equivalents of esters 21, respectively. Finally, secondary amino group deprotection is carried out using a 20% solution of piperidine (Pip) in DCM, following routine purification of the fully protected intermediates by FCC, if necessary.

Figure 5:
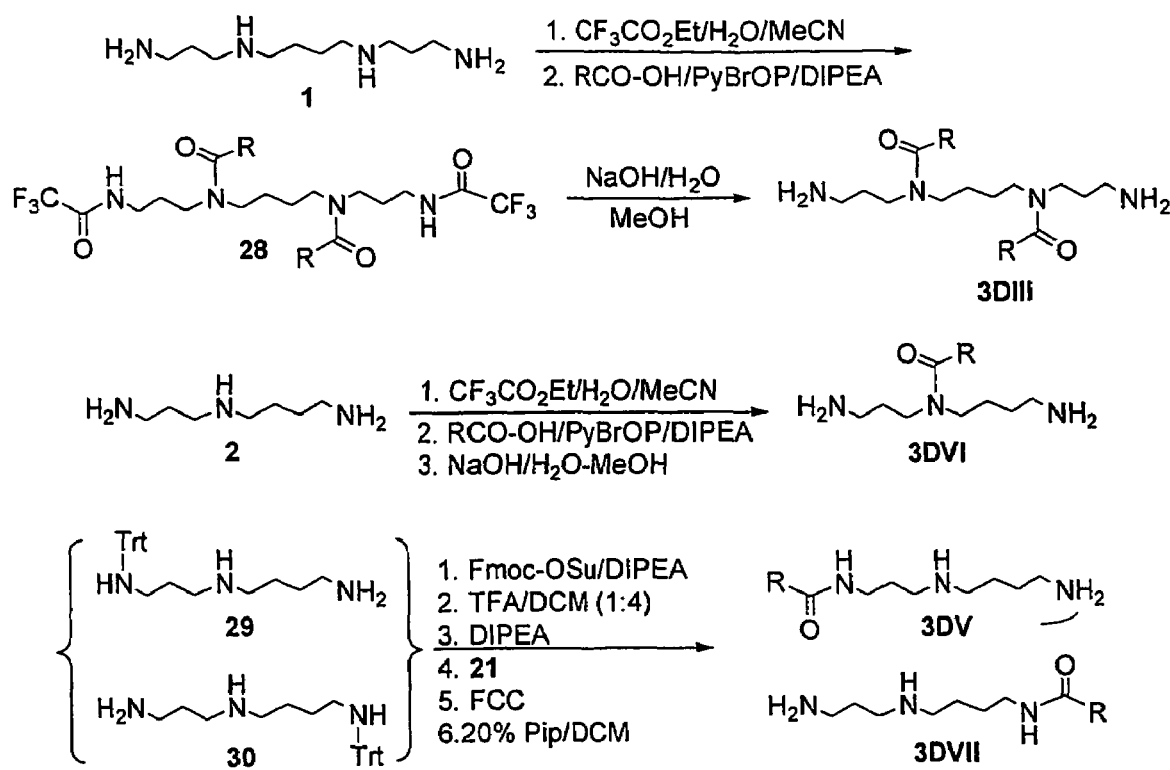
FIG. 5: Synthetic schemes for the preparation of the $N^4,N^9$-bisamide of spermine and of all three N-monoamides of spermidine with acidic retinoids

The preparation of polyamines acylated at their secondary amino functions by activated acidic retinoid derivatives is exemplified in FIG. 5 with the preparation of the spermine conjugates 3DIII and described in detail under the EXAMPLE 4. Thus, selective trifluoroacetylation of the primary amino functions (O'Sullivan and Dalrymple, TETRAHEDRON LETT., 36, 3451 (1995); Blacklock et al, TETRAHEDRON LETT., 36, 7357 (1995); Krakowiak and Bradshaw, SYNTH. COMMUN., 28, 3451 (1998); Blagbrough et al, TETRAHEDRON, 56, 3439 (2000)) with $CF_3CO_2Et$ followed by acylation of the remaining amino functions with the acidic retinoid in the presence of the powerful coupling agent bromotripyrrolidinophosphonium hexafluorophosphate (PyBrOP) and $^iPr_2NEt$ leads to the fully protected spermine derivatives 28, from which the projected conjugates 3DIII are obtained through alkaline hydrolysis. Using the same methodology described in detail under and EXAMPLE 5, the $N^4$-monoacylated spermidine conjugates 3DVI were obtained (FIG. 5), whereas the other two possible regioisomers 3DV and 3DVII became available through the corresponding $N^1$(29)- and $N^8$(30)-tritylspermidines, according to the methodology also described in FIG. 5 and detailed under the EXAMPLE 6. The preparation of the former precursor has been already described (Papaioannou et al, TETRAHEDRON LETT., 42, 1579 (2001)) whereas the latter was readily obtained through coupling of the chloride Fmoc-NH$(CH_2)_2$COCl (Papaioannou et al, TETRAHEDRON LETT., 36, 5187 (1995)) with N-tritylputrescine in the presence of $^iPr_2NEt$, followed by routine removal of Fmoc group and finally $LiAlH_4$-mediated reduction.

Figure 4:
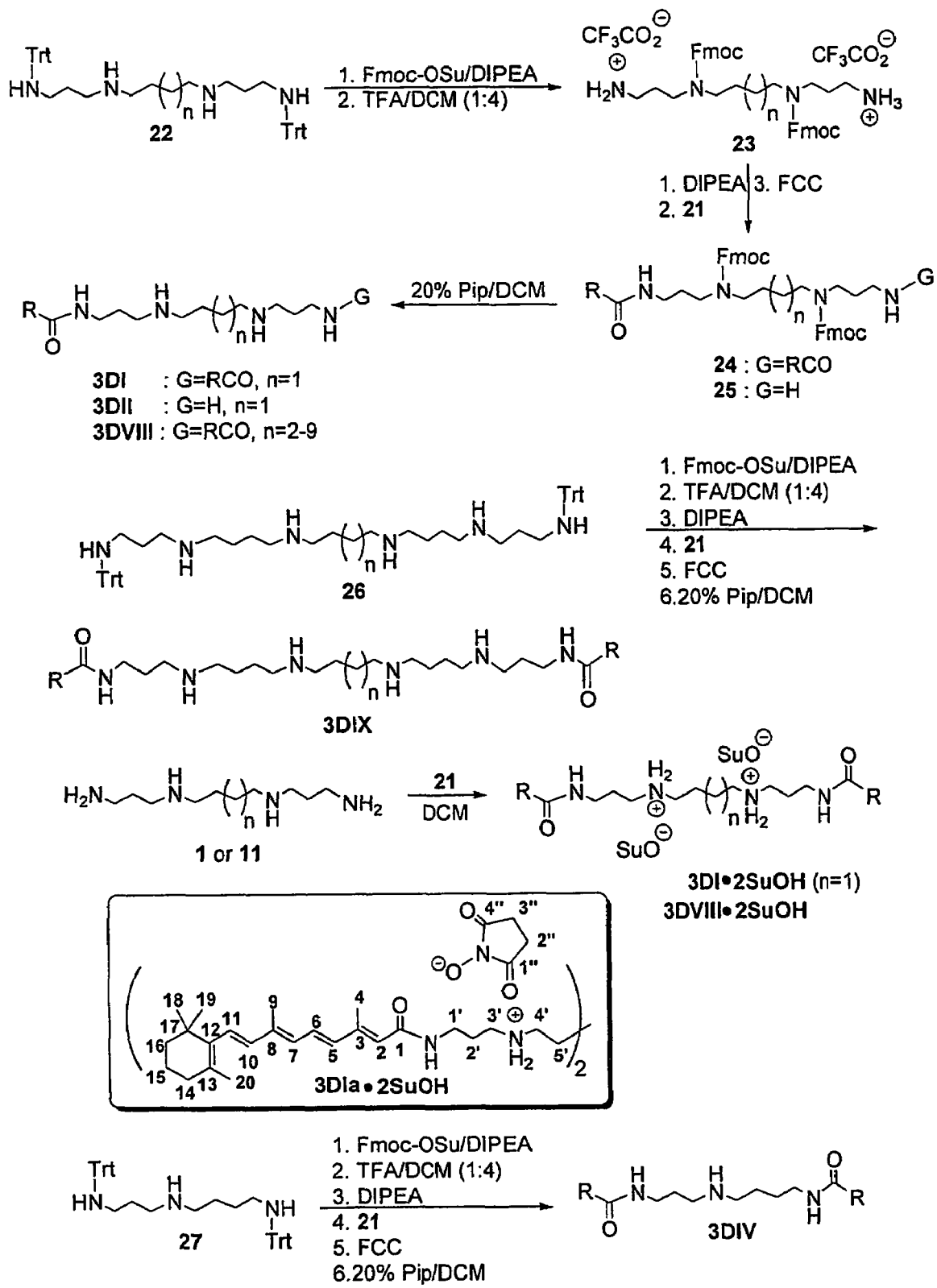
FIG. 4: Synthetic schemes for the preparation of $N^\alpha$-mono- and $N^\alpha$, $N^\omega$-bisamides of linear polyamines with acidic retinoids
Figure 6:
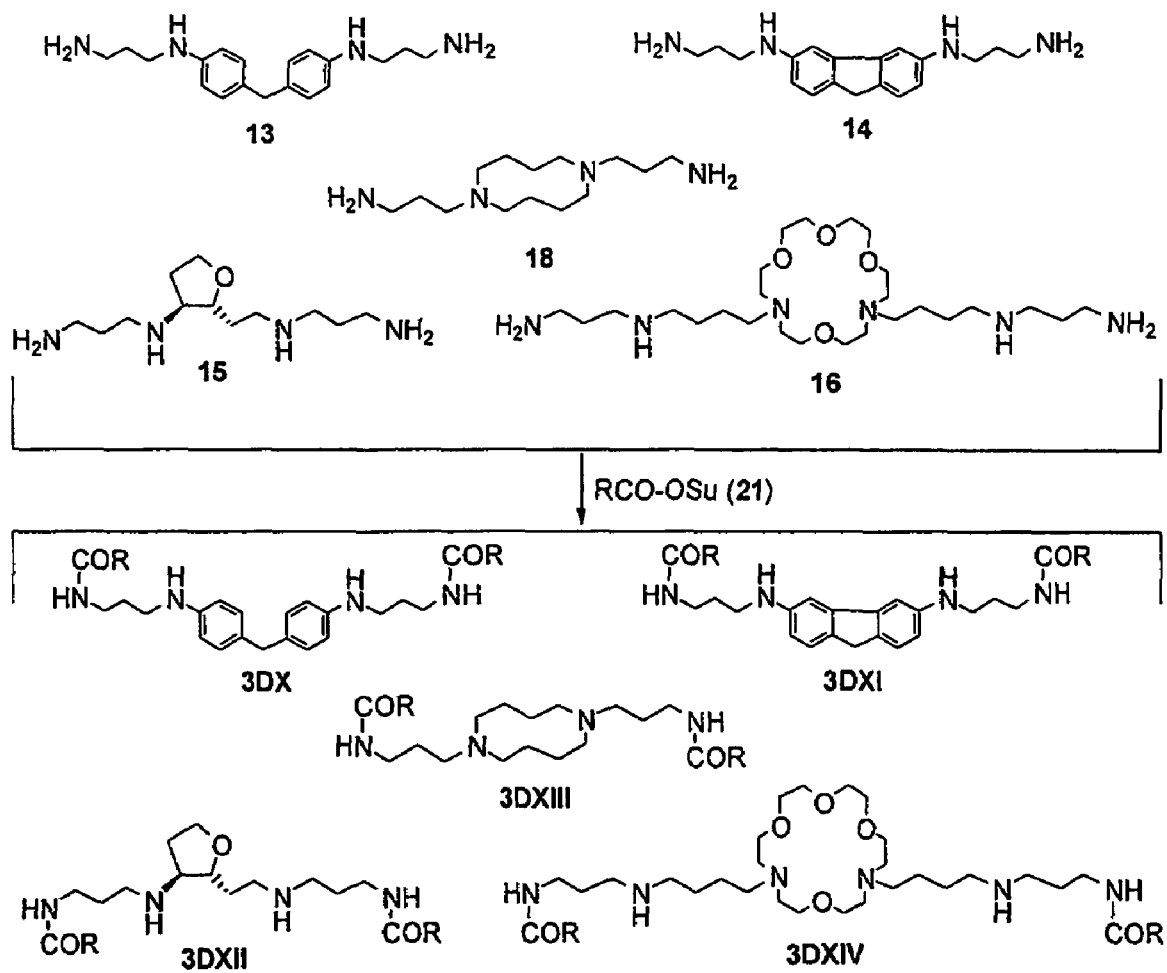
FIG. 6: Synthetic schemes for the preparation of $N^\alpha,M^\omega$-bisamides of conformationally restricted tetra- and hexa-amines with acidic retinoids
Figure 7:
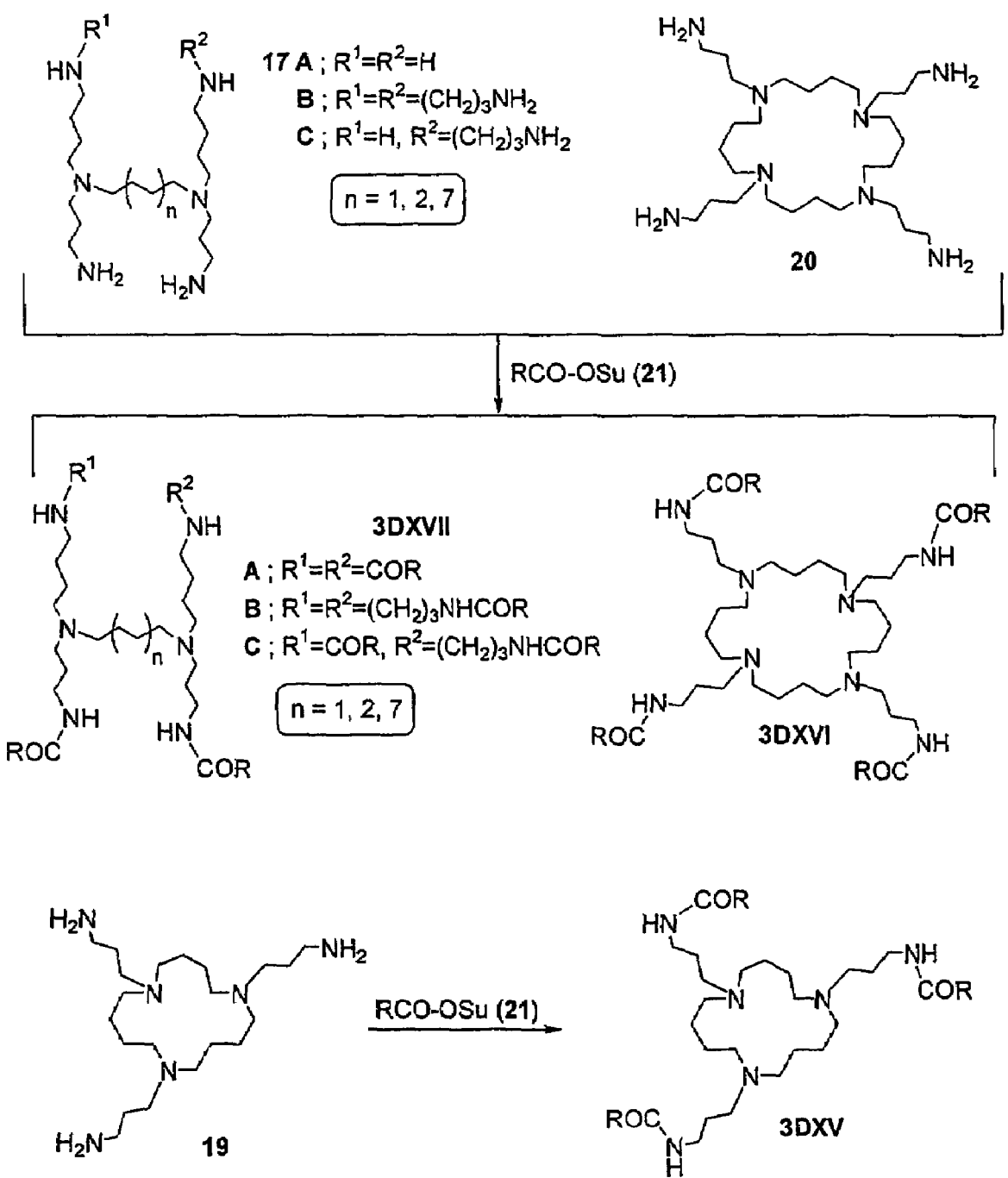
FIG. 7: Synthetic schemes for the preparation of polyamides symmetric and asymmetric dimers of spermine and spermidine and of cyclic hexa- and octa-amines and of with acidic retinoids

The preparation of the polyamine bisamides 3DX-3DXIV incorporating two retinoid residues at their primary amino functions is described in FIG. 6 and is identical to the direct preparation of the conjugates 3DVIII.2SuOH (FIG. 4). It involves simple treatment of the tetra-amines 13-15 and 18 and the hexa-amine 16 with two molar equivalents of the succinimidyl esters 21. In case the free bases are not readily available, the corresponding polytrifluoroacetate salts are used instead and $^iPr_2NEt$ for their in situ neutralization (see EXAMPLE 2, direct method B). Syntheses of the polyamines 13-16 and 18, used as starting materials in these preparation, have been already described by one of the inventors (Papaioannou et al, TETRAHEDRON LETT., 43, 2593 (2002) and Papaioannou et al, in 'Drug Discovery and Design: Medical Aspects', J. Matsoulkas and T. Mavromoustakos (Eds.), IOS Press, Amsterdam, 2002,. in press). Finally, the preparation of the polyamine tri(3DXV)- and tetra(3DXVI and 3DXVIIA-C)-amides incorporating three and four retinoid residues, respectively, at their primary amino functions is described in FIG. 7. These syntheses involve the coupling of the corresponding polyamines 19 and 17 and 20 with three and four molar equivalents, respectively, of succinimidyl esters 21. The synthesis of polyamines 17 (Papaioannou et al, TETRAHEDRON LETT., 43, 2597 (2002)) and 19 and 20 (Papaioannou et al, TETRAHEDRON LETT., 43, 2593 (2002)) has been also recently described.

Biological Evaluation

Figure 8:
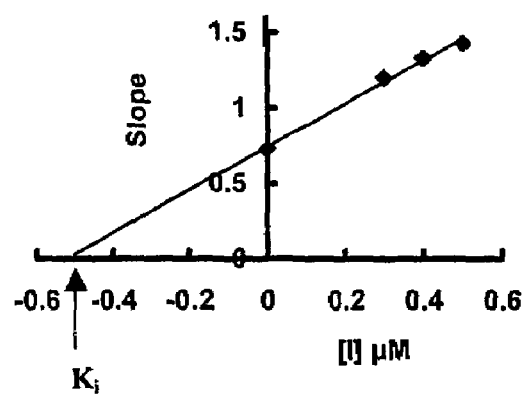
FIG. 8: Double reciprocal plot (1/v versus 1/[pre-tRNA]) for RNase P reaction in the presence of $N^1,N^{12}$-$RA_2$-Spermine. The reaction was carried out at the indicated concentrations in the presence or absence of inhibitor. All reactions were carried out at 37° C. in 20 μl buffer D in the presence of 10% DMSO. (♦) without inhibitor, with $N^1$, $N^{12}$-$RA_2$-Spermine at (■) 3 μM, (▲) 4 μM, (●) 5 μM. Top panel: Replot of the slopes of the double reciprocal lines versus inhibitor (I) concentrations.
Figure 8:
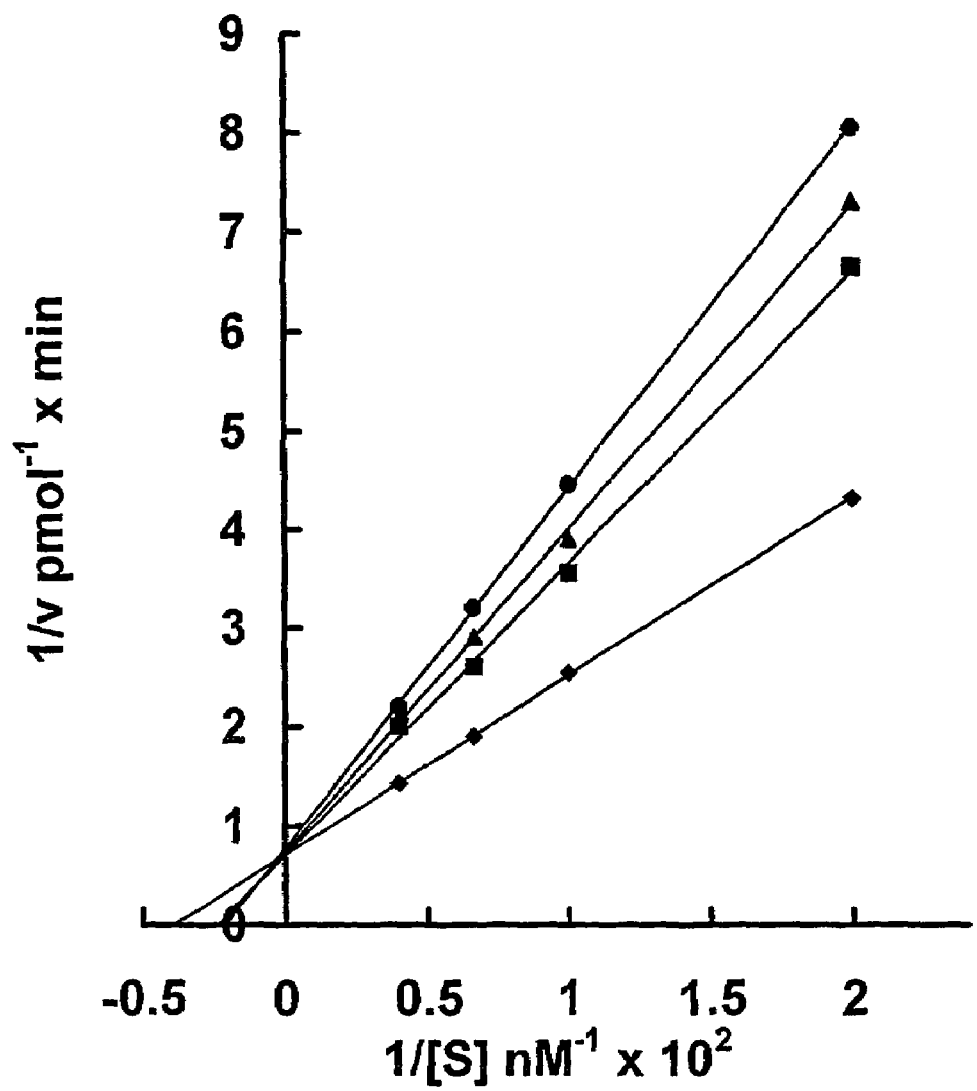
Figure 9:
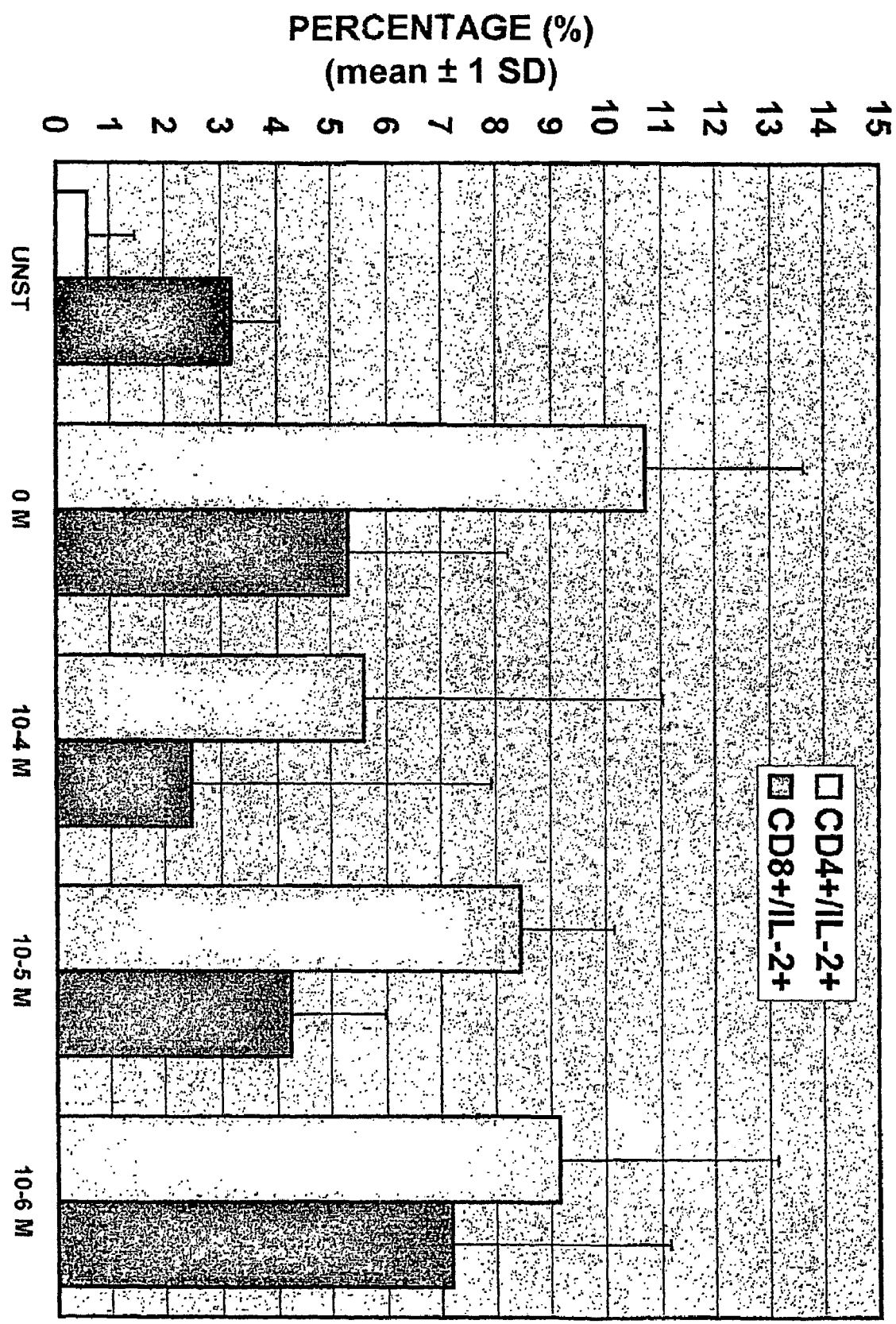
FIG. 9: Effect of $N^1,N^{12}$-$RA_2$-SPM on the percentage of CD4+/IL-2+ and CD8+/IL-2+ peripheral blood mononuclear cells.

Inhibitory Activity on RNAse P. We have developed a method by which we can estimate rapidly the biological activity of the polyamine-retinoid conjugates. This method is based on the effect of the polyamine-retinoid conjugates on RNase P activity and is described in detail under the EXAMPLE 7. All synthesized conjugates were screened for their effect on RNase P activity by constructing the dose response curves. From the dose response curves the $IC_{50}$ value (the concentration of conjugate at which the product formation is reduced by 50%) is calculated (Papadimou et al., J. BIOL. CHEM. 273, 24375 (1998)), which is a first and quite reliable measure for the potency of retinoid analogues. The accurate estimation of the inhibitory potency on the RNAse P of the strongest polyamine-retinoid conjugates were elucidated by detailed kinetic analysis of their effect on *D. discoideum* or human epidermal keratinocytes RNase P activity. In order to carry out such analysis, the initial velocity in the presence or absence of the conjugate was determined from the initial slopes of time plots. The data plotted in double reciprocal plots (1/v versus 1/[S]) with increasing concentrations of polyamine-retinoid conjugates and the $K_i$ values (the dissociation constant of the inhibitor (I), where I is a polyamine-retinoid conjugate, with the enzyme) were determined from the replots of the slopes of the double reciprocal plots versus the inhibitor's concentration (Papadimou et al., J. BIOL. CHEM. 273, 24375 (1998), Papadimou et al., SKIN PHARMACOL. APPL. SKIN PHYSIOL. 13, 345 (2000)). These replots lead to the graphical determination of $K_i$ values from the negative intercept of the line with the I-axis. FIG. 8 shows the double reciprocal plot and the slope replot for $N^1,N^{12}$-bisretinoylspermine. Similar plots were constructed for all conjugates. The $K_i$ value is a very good measure for the accurate potency of the polyamine-retinoid conjugates. The $K_i$ values of the effect of the most potent polyamine-retinoid conjugates on *D. discoideum* RNase P activity are presented in Table 1, below, in comparison to known natural and synthetic retinoids and arotinoids. Similar $K_i$ values were obtained with normal human epidermal keratinocytes RNase P.

Anti-Inflammatory Activity. Preliminary experiments were performed to determine the optimum conditions for IL-2 and IFN-γ detection intracellularly (data not shown), which mainly involved determination of brefeldin, ionomycin and PMA concentrations and duration of the incubation period and of the brefeldin presence. It was determined that the addition at the initiation of the incubation period of 5 ng/ml of PMA in combination with 250 ng/ml of ionomycin, as well as the addition for the last 2 h of a 4 h incubation period of 5 μg/ml of brefeldin, were accompanied by a peak release of both cytokines in the intracellular space.

PBMC incubation in the presence of PMA/ionomycin was accompanied in all experiments by a significant up-regulation of the IL-2 and IFN-γ expression compared to the unstimulated cultures. This was manifested on both CD4+ and CD8+ lymphocytes and was evidenced both as an up-regulation of the lymphocyte percentage, as well as an upregulation of the fluorescence intensity. Furthermore, it was observed that CD4+ lymphocytes were the major producers of IL-2, whereas CD8+ lymphocytes were mostly producing IFN-γ.

Addition of a polyamine-retinoid conjugate, e.g. $N^1,N^{12}$-$RA_2$-SPM, at the initiation of the culture, at concentrations $10^{-4}$, $10^{-5}$ and $10^{-6}$ M, had a variable effect on PMA/ionomycin-induced IL-2 levels (see EXAMPLE 8). The highest concentration of the conjugate ($10^{-4}$ M) caused a decrease in the percentage of CD4+/IL-2+ and CD8+/IL-2+ cells, as well as in the intensity of fluorescence, whereas the other two concentrations had a minimal or no effect. At a concentration of $10^{-4}$ M, the polyamine-retinoid conjugate induced a decrease in CD4+/IFN-γ+ cell intensity of fluorescence and percentage of CD8+/IFN-γ+ cells, whereas the other two lower concentrations revealed a minimal or no effect (FIGS. 9-12)

TABLE 1

Selected equilibrium constants derived from primary and secondary plots.

| Retinoids | $K_i^a$ (μM) | Polyamine conjugates with retinoids (new compounds) | $K_i^a$ (μM) |
|---|---|---|---|
| Retinol | 1,475 | $N^1$-RA-Spermine (3DIIa) | 2.4 |
| all-trans-Retinoic acid (RA) | 15 | $N^1,N^{12}$-$RA_2$-Spermine (3DIa) | 0.5 |
| Isotretinoin | 20 | $N^4,N^9$-$RA_2$-Spermine (3DIIIa) | 1.1 |
| Acitretin (Aci) | 8 | $N^1$-Aci-Spermine (3DIIb). 3 HCl | 2.45 |
| Ro 13-7410 | 45 | $N^1,N^{12}$-$Aci_2$-Spermine (3DIb). 2 HCl | 0.95 |
| Ro 15-0788 | 2,800 | | |
| Ro 15-1570 | 3,600 | | |
| Ro 13-6298 | 4,350 | | |
| RA + Spermine | 15 | | |

$^a$The $K_i$ values are calculated from the negative intercept of the slope replots (see FIG. 8)

EXAMPLES

Experimental

Capillary melting points were taken on a Büchi SMP-20 apparatus and are uncorrected. IR spectra were recorded as KBr pellets or with neat oily samples on a Perlkin-Elmer 16PC FT-IR spectrophotometer. $^1$H-NMR spectra were obtained at 400.13 MHz, on a Bruker Avance 400 DPX spectrometer. Electron-Spray Ionization (ESI) mass spectra were obtained on a Micromass-Platform LC spectrometer for solutions of the measured compounds in MeOH. Microanalyses were performed on a Carlo Erba EA 1108 Elemental Analyzer. All new compounds gave satisfactory microanalytical data to within ±0.3 of the calculated values. Flash Column Chromatography (FCC) was performed on Merck silica gel 60 (230-400 mesh) and Thin layer Chromatography (TLC) on Merck silica gel $F_{254}$ films (0.2 mm) precoated on aluminium foil. The solvent or solvent systems used were : (A) PhMe/EtOAc (95:5), (B) PhMe/EtOAc (9:1), (C) PhMe/EtOAc (7:3), (D) PhMe/EtOAc (1:1), (E) $CH_2Cl_2$/MeOH (9:1), (F) $CHCl_3$/MeOH (9:1), (G) $CHCl_3$/MeOH/conc. $NH_3$ (7:3:0.3), (I) $CHCl_3$/MeOH/conc. $NH_3$ (6:4:0.4), (J) $CHCl_3$/MeOH/conc. $NH_3$ (5:5:0.5). Spots were visualized with UV light at 254 nm and ninhydrin. All solvents used were dried according to standard procedures prior to use. Experiments involving retinoids were routinely conducted under an atmosphere of Ar and with protection from light. Drying of solutions was effected with anhydrous $Na_2SO_4$, whereas evaporation of the solvents was performed under reduced pressure in a rotary evaporator at a bath temperature not exceeding 40° C.

The examples below are given so as to illustrate the practice of this invention. They are not intended to limit or define the entire scope of the invention.

Example 1

Preparation of Succinimidyl Retinoate (21a)

To an ice-cold solution of all-trans-retinoic acid (5) (3.00 g, 10 mmol) in dry THF or DMF (30 ml) was added sequentially HOSu (1.72 g, 15 mmol) and DCC (2.48 g, 12 mmol) and the resulting mixture was stirred for an additional 30 min at 0° C. and for overnight at ambient temperature. The precipitated DCU was filtered off and washed several times with EtOAc. The combined filtrates were washed sequentially with an ice-cold 5% aqueous (aq.) $NaHCO_3$ solution, $H_2O$ and twice with brine. Drying, followed by filtration and evaporation of the solvent left a residue. FCC of the residue using as eluant the solvent system A, pooling the fractions containing pure product, evaporation and trituration with $Et_2O$ gave 3.38 g (85%) of yellowish crystalline ester 21a following overnight refrigeration. $R_f(A)$ : 0.24. M.p. : 173-76° C. FT-IR ($cm^{-1}$) : 1758, 1732, 1626, 1595, 1574, 1558. 400 MHz $^1$H-NMR ($CDCl_3$) : δ 7.152 (1H, dd, J 11.6 and 15.2 Hz, H-6), 6.352 (2H, d, J 15.2 Hz, H-5 and H-11), 6.176 (1H, d, J 16.0 Hz, H-10), 6.166 (1H, d, J 10.3 Hz, H-7), 5.954 (1H, s, H-2), 2.852 (4H, br. S, H-2' and H-3'), 2.382 (3H, s, H-4), 2.030 (3H, s, H-9), 2.030 (2H, m, H-14), 1.722 (3H, s, H-20), 1.613 (2H, m, H-15), 1.472 (2H, m, H-16), 1.035 (6H, s, H-18 and H-19) ppm. Elemental analysis based on $C_{24}H_{31}NO_4$ ((Calc.) Found) : C, (72.52) 72.69; H, (7.86) 7.72; N, (3.52) 3.28.

Example 2

Preparation of $N^1,N^{12}$-Bisretinoylspermine (3DIa)

Direct Method A:

To an ice-cold solution of spermine (1) (0.55 g, 2.7 mmol) in dry $CH_2Cl_2$ (25 ml) was added ester 21a (1.99 g, 5 mmol). The resulting solution was stirred for an additional hour at 0° C. and then placed in the refrigerator for overnight. The precipitated product was filtered off, washed on the filter with ice-cold $CH_2Cl_2$ and dried under reduced pressure to give 2.02 g (80%) of the bishydroxysuccinimidate salt of 3DIa as a yellow solid.

$R_f(I)$ : 0.40 (free base) and 0.13 (HOSu). M.p.: 149-52° C. FT-IR ($cm^{-1}$) : 3430, 3317, 1674, 1647. ESI-MS (m/z) : 768.74 (MH), 767.75 (M), 485.56 ($R^1$CO-SPM+H), 580.02 (MH-$C_{14}H_{20}$), 384.72 ($MH_2/2$). 400 MHz $^1$H-NMR ($d_6$-DMSO): δ 8.040 (2H, unresolved t, NHCO), 6.912 (2H, dd, J 12.1 and 14.2 Hz, H-6), 6.33-6.15 (8H, m, H-5, H-7, H-10, H-11), 5.840 (2H, s, H-2), 5.780 (4H, s, $H_2N^+$), 3.150 (4H, unresolved q, H-1'), 2.529 (16H, m, H-3', H-4', H-2", H-3"), 2.290 (6H, s, H-4), 2.024 (4H, unresolved t, H-14), 1.976 (6H, s, H-9), 1.704 (6H, s, H-20), 1.598 (8H, m, H-15, H-2'), 1.474 (8H, m, H-16, H-5'), 1.032 (12H, s, H-18, H-19) ppm. Elemental analysis based on $C_{58}H_{88}N_6O_8$ ((Calc.) Found) : C, (69.85) 69.56; H, (8.89) 8.97; N, (8.43) 8.62.

Direct Method B:

When $CHCl_3$ was used as the reaction solvent, complete solution of reactants and products was observed. The reaction was found complete (by TLC) within 30 min at 0° C. and then it was worked-up by diluting the resulting solution with EtOAc, washing sequentially twice with a 5% aq. $NaHCO_3$ solution and twice with water. The organic phase was then dried and evaporated to leave crude product, which was purified by FCC using as eluant the solvent system I to give pure free 3DIa, as a yellow powder, in 75% yield.

Alternatively and in order to facilitate the work-up and purification by FCC procedures, after the diacylation of spermine, in situ protection of the remaining free secondary amino functions with the trifluoroacetyl(Tfa) group, by treating the reaction mixture with trifluoroacetic anhydride ($Tfa_2O$) in the presence of $Et_3N$ for 5 min at 0° C. και for 30 min at ambient temperature, takes place. Then, the fully protected product is subjected initially to purification with FCC and finally to removal of the temporary protecting groups by treating with $K_2CO_3$ at refluxing $MeOH/H_2O$ (6:0.5) for 30 min, giving the free product 3DIa in 68% total yield.

Indirect Method:

To an ice-cold solution of $N^1,N^{12}$-$Trt_2$-SPM (22a; n=1) (2 g, 3 mmol) in dry $CH_2Cl_2$ (30 ml) was added sequentially $^iPr_2NEt$ (1.4 ml, 8 mmol) and Fmoc-OSu (2.2 g, 8 mmol). After 30 min at ambient temperature, the reaction mixture was diluted with $CH_2Cl_2$ (100 ml) and washed sequentially twice with a 5% aq. $NaHCO_3$ solution and twice with water. Drying and evaporation of the solvent left a residue which was subjected to FCC using as eluant the solvent system B to give 3.26 g of pure product $N^4,N^9$-$Fmoc_2$-$N^1$, $N^{12}$-$Trt_2$-SPM as a foam. This was then treated with a solution (20 ml) of trifluoroacetic acid (TFA) in $CH_2Cl_2$ (1:4) for 30 min at 0° C. Evaporation of the solvent left a residue which was triturated with $Et_2O$/hexane (1:1) and refrigerated overnight. The supernatant liquid was poured off and the residue was subjected to FCC using as eluant the solvent system E to give 1.8 g (69% yield based on 22a) of the bistrifluoroacetate salt of $N^4,N^9$-$Fmoc_2$ -SPM (23a) as a foam.

To an ice-cold solution of 23a (0.88 g, 1 mmol) in 2 ml $DMF/CHCl_3$ (1:1) was added sequentially $^iPr_2NEt$ (0.7 ml, 4 mmol) and 'active' ester 21a (0.79 g, 2 mmol). After 1 h at ambient temperature, the reaction mixture was diluted with 50 ml EtOAc and washed once with a 5% aq. $NaHCO_3$ solution and twice with water. Drying, evaporation and FCC with the eluant D gave the intermediate 24a. This was then treated with a solution (10 ml) of piperidine (Pip) in $CH_2Cl_2$ (1:4) for 15 min at ambient temperature. Evaporation of the solvent, trituration of the residue with $Et_2O$, refrigeration and finally filtration gave 0.57 g (74%) of 3DIa.

Example 3

Preparation of $N^1$-retinoylspermine (3DIIa)

To an ice-cold solution of 23a (0.88 g, 1 mmol) in 2 ml $DMF/CHCl_3$ (1:1) was added $^iPr_2NEt$ (0.4 ml, 2.3 mmol) and then 'active' ester 21a (0.32 g, 0.8 mmol) in small portions within 1 h. After additional 30 min at ambient temperature, the reaction mixture was diluted with 50 ml EtOAc and washed once with a 5% aq. $NaHCO_3$ solution and twice with water. Drying, evaporation and FCC of the residue with the eluant F gave the intermediate 25a with $R_f(F)$ 0.15. This was then treated with a solution (10 ml) of Pip in $CH_2Cl_2$ (1:4) for 30 min at ambient temperature. Evaporation of the solvent under reduced pressure, trituration of the residue with $Et_2O$ and refrigeration gave a precipitate. Finally, filtration and evaporation of the filtrate gave 0.18 g (47%) of 3DIIa as a yellowish foam. ESI-MS (m/z) : 485.86 (MH).

It should be noted that in the above described reaction of compound 23a with ester 21a, considerable amounts of the corresponding diacylated spermine were also formed, but this by-product is easily separated from the monoacylated spermine derivative 25a, during the afore mentioned FCC. The trishydrochloride salt of 3DIIa was also obtained, as a yellowish powder, by triturating an ice-cold solution of the free base in MeOH with an ice-cold solution of 1.2 N solution of gaseous HCl in anhydrous MeOH, followed by immediate precipitation of the thus formed salt with $Et_2O$.

Example 4

Preparation of $N^4,N^9$-Bis(All-Trans-Retinoyl)Spermine (3DIIIa)

To an ice-cold solution of the bistrifluoroacetate salt of $N^1,N^{12}$-bistrifluoroacetylspennine (0.32 g, 0.5 mmol) in anhydrous $CHCl_3$ (1 ml) was added $^iPr_2NEt$ (0.7 ml, 4 mmol) and a mixture consisted of all-trans-retinoic acid (0.3 g, 1 mmol) and PyBrOP (0.6 g, 1.28 mmol) in small portions over a period of 1 h. After 30 min at ambient temperature, the reaction mixture was diluted with CHCl$_3$ and washed sequentially with an ice-cold 5% aq. NaHCO$_3$ solution (twice) and water (twice). Drying and evaporation left a residue from which pure intermediate 28a (R=R$^1$) was obtained through FCC using the solvent system D as eluant. Intermediate 28a was dissolved in 4 ml MeOH and treated with 0.4 ml of a 4.75 N aq. NaOH solution for 2 h at ambient temperature. MeOH was then removed under reduced pressure and the residue was taken up in 20 ml water and extracted twice with CH$_2$Cl$_2$. The combined organic layers were washed twice with brine, dried and evaporated to leave 0.16 g (40%) of pure 3DIIIa as a yellow powder. R$_f$(J): 0.26. FT-IR (cm$^{-1}$): 3434, 1620. ESI-MS (m/z): 790.30 (ANa), 768.31 (MH). Elemental analysis based on C$_{58}$H$_{88}$N$_6$O$_8$ ((Calc.) Found): C, (69.85) 70.08; H, (8.89) 8.60; N, (8.43) 8.21.

Example 5

Preparation of N$^4$-Acitretinoylspermidine (3DVIb)

A solution of spermidine (2) (0.73 g, 5 mmol) and ethyl trifluoroacetate (2 ml, 17,5 mmol) in acetonitrile (15 ml) containing 0.11 ml (6 mmol) H$_2$O was refluxed for overnight and then the solvent evaporated to leave 2.1 g (92% yield) of the monotrifluoroacetate salt of N$^1$,N$^8$-bistrifluoroacetyl-spermidine as a foam, which was used as such into the next step. Thus, to an ice-cold solution of this salt (0.50 g, 1.1 mmol) in anhydrous DMF (1.4 ml) and CHCl$_3$ (1 ml) was added $^i$Pr$_2$NEt (0.7 ml, 4 mmol) followed by acitretinoin (0.34 g, 1.06 mmol) and PyBrOP (0.82 g, 1.76 mmol). The reaction mixture was stirred at 0° C. for 30 min and at ambient temperature for overnight. Then diluted with EtOAc and washed once with an ice-cold 5% aq. NaHCO$_3$ solution and twice with cold H$_2$O, dried and evaporated to leave a residue. From this residue, 0.60 g (86%) of the fully protected 3DVIb was obtained as a yellow oil after FCC purification using as eluant the solvent system D. R$_f$(D) 0.26. The product had ESI-MS (rn/z): 668.23 (MNa), 645.92 (MH). Fully protected 3DVIb (0.60 g, 1 mmol) was dissolved in MeOH (60 ml) and H$_2$O (6 ml) and K$_2$CO$_3$ (0.52 g, 4 mmol) were added and the resulting mixture was refluxed for 90 min. Then filtered hot and concentrated to dryness. The residue was subjected to FCC, using the solvent system G as eluant, and the fractions with R$_f$(G) 0.12 were pooled and evaporated to leave pure product 3DVIb (0.38 g, 83%) as a yellowish foam. The product had ESI-MS: 454.33 (MH).

Example 6

Preparation of N$^8$-Acitretinoylspermidine (3DVIIb)

To an ice-cold solution of N$^8$-Trt-SPD (30) (0.5 g, 1.3 mmol) was added $^i$Pr$_2$NEt (0.5 ml, 2.6 mmol) and Fmoc-OSu (0.5 g, 2.6 mmol). After 30 min at 0° C., the reaction mixture was diluted with EtOAc and washed once with an ice-cold 5% aq. NaHCO$_3$ solution, then H$_2$O and finally brine and dried. Filtration, evaporation and FCC of the residue using the solvent system B as the eluant, gave pure product which was immediately treated with 10 ml of a solution of TFA in CH$_2$Cl$_2$ (3:7) for 30 min at 0° C. Solvent evaporation, trituration of the residue with Et$_2$O and rejection of the supernatant liquid left 0.41 g (45% yield) of the trifluoroacetate salt of N$^1$,N$^4$-Fmoc$_2$-SPD. R$_f$(E) 0.21. ESI-MS (m/z): 704.64 (MH).

To an ice-cold solution of this salt (0.34 g, 0.48 mmol) in DMF (2 ml) was added $^i$Pr$_2$NEt (0.2 ml, 1.2 mmol) and the 'active' ester 21b (0.2 g, 0.48 mmol). After 1 h at 0° C. and 1 h at ambient temperature, the reaction mixture was diluted with EtOAc and washed twice with an ice-cold 5% aq. NaHCO$_3$ solution and twice with H$_2$O, dried and evaporated to dryness. The residue was subjected to FCC, using as eluant the solvent system C to give 0.31 g (72% yield) of the fully protected 3DVIIb as a yellowish foam. R$_f$(B) 0.27. ESI-MS (m/z) : 899.08 (MH). This intermediate (0.3 g, 0.33 mmol) was subsequently treated with a 20% solution of Pip in CH$_2$Cl$_2$ for 2 h at ambient temperature. The solvent was then evaporated and the residue was triturated with Et$_2$O. The supernatant liquor was discarded and this procedure was repeated. Finally, drying of the residue left 0.14 g (93%) of pure product 3DVIIb as a yellow foam. ESI-MS (m/z): 455.02 (MH).

Example 7

Biological Evaluation of Compounds as RNase P Inhibitors

RNase P assays were carried out at 37° C. in 20 μbuffer D (50 mM Tris/HCl pH 7.6, 10 mM NH$_4$Cl, 5 mM MgCl$_2$ and 5 mM dithiothreitol) if RNase P isolated from *D. discoideum* was used (Stathopoulos et al.; EUR. J. BIOCHEM. 228, 976 (1995)) or buffer K (50 mM Tris/HCl pH 7.5, 100 mM NH$_4$Cl, 5 mM MgCl$_2$ and 5 mM dithiothreitol) if RNase P isolated from human epidermal keratinocytes was used (Drainas et al, unpublished data), containing 2-5 finol pre-tRNA$^{ser}$ substrate (an in vitro labeled transcript of the *Schizosaccharoinyces pombe* tRNA$^{ser}$ gene supSI) and 1.3 μg protein from the RNase P fraction. Stock solutions of retinoids (natural or synthetic), are prepared in 100% dimethylosulfoxide (DMSO). When retinoids are used, enzyme assays are carried out in the presence of 10% DMSO. The reactions were stopped by addition of 5 μl stop dye (80% formamide, 50 mM EDTA, 0.1% bromophenol blue, 0.1% xylene cyanol). Reaction products were resolved on a denaturing 10% polyacrylamide/8 M urea gel and visualized by autoradiography without drying. Activity was quantified by Cerenkov counting of excised gel slices.

Example 8

Biological Evaluation of Compounds as Anti-Inflammatory Agents

For the purpose of the study, peripheral blood mononuclear cells (PBMC) from ten healthy volunteers (age 33-52 yrs) were incubated in 1 ml volume (RPMI 1640/10% FCS) for varying time periods at 37° C. in a CO$_2$ (5%) incubator in the presence or absence of PMA (Sigma, St Louis, Mo.), ionomycin (Sigma, St Louis, Mo.) and/or the polyamine-retinoid conjugate (10$^{-4}$, 10$^{-5}$, 10$^{-6}$ M) as well as a protein transport inhibitor, brefeldin (Sigma, St Louis, Mo.) to prevent cytokine secretion in the extracellular space.

Figure 10:
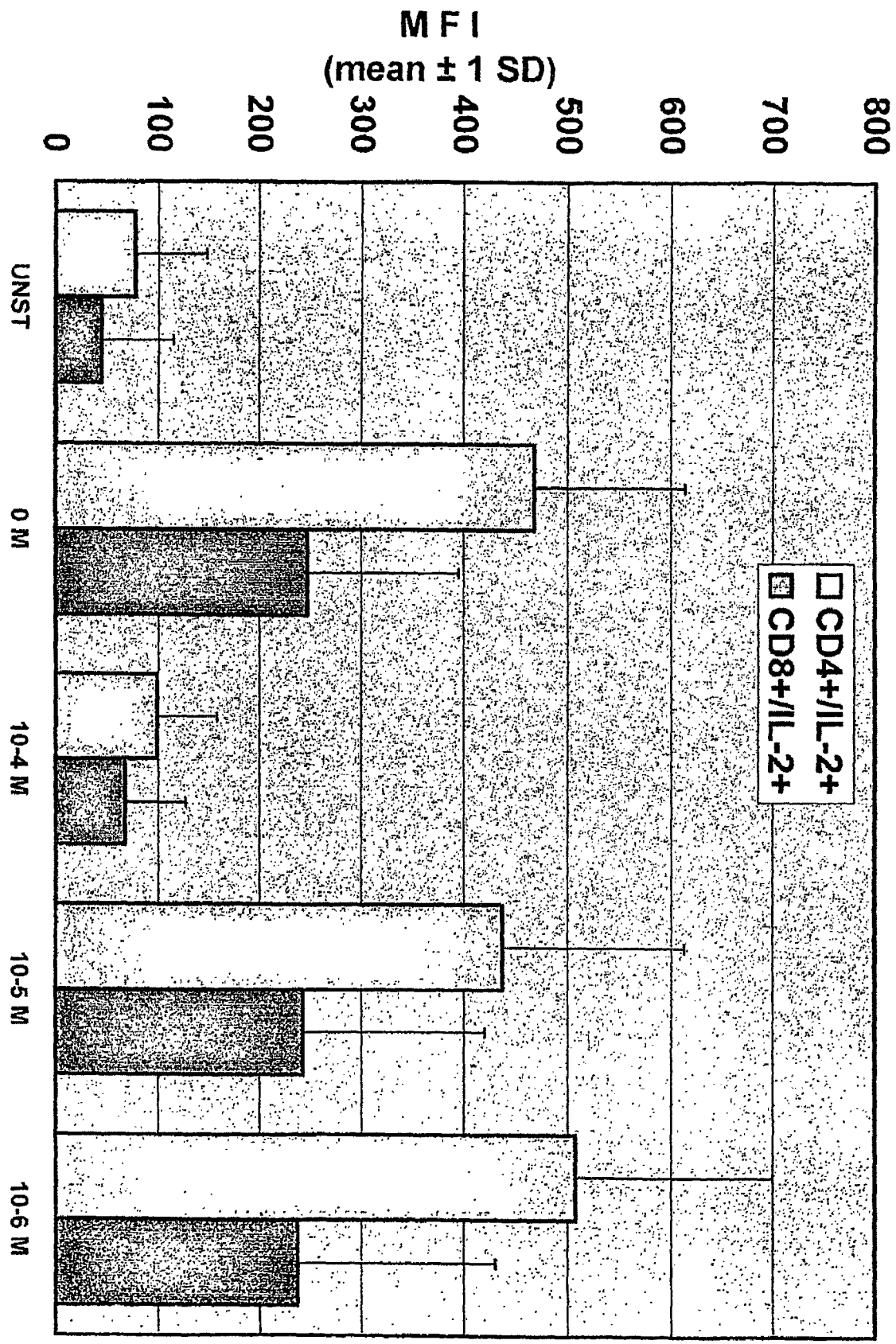
FIG. 10: Effect of $N^1$, $N^{12}$-$RA_2$-SPM on the mean fluorescence intensity (MFI) of CD4+/IL-2+ and CD8+/IL-2+ peripheral blood mononuclear cells.
Figure 11:
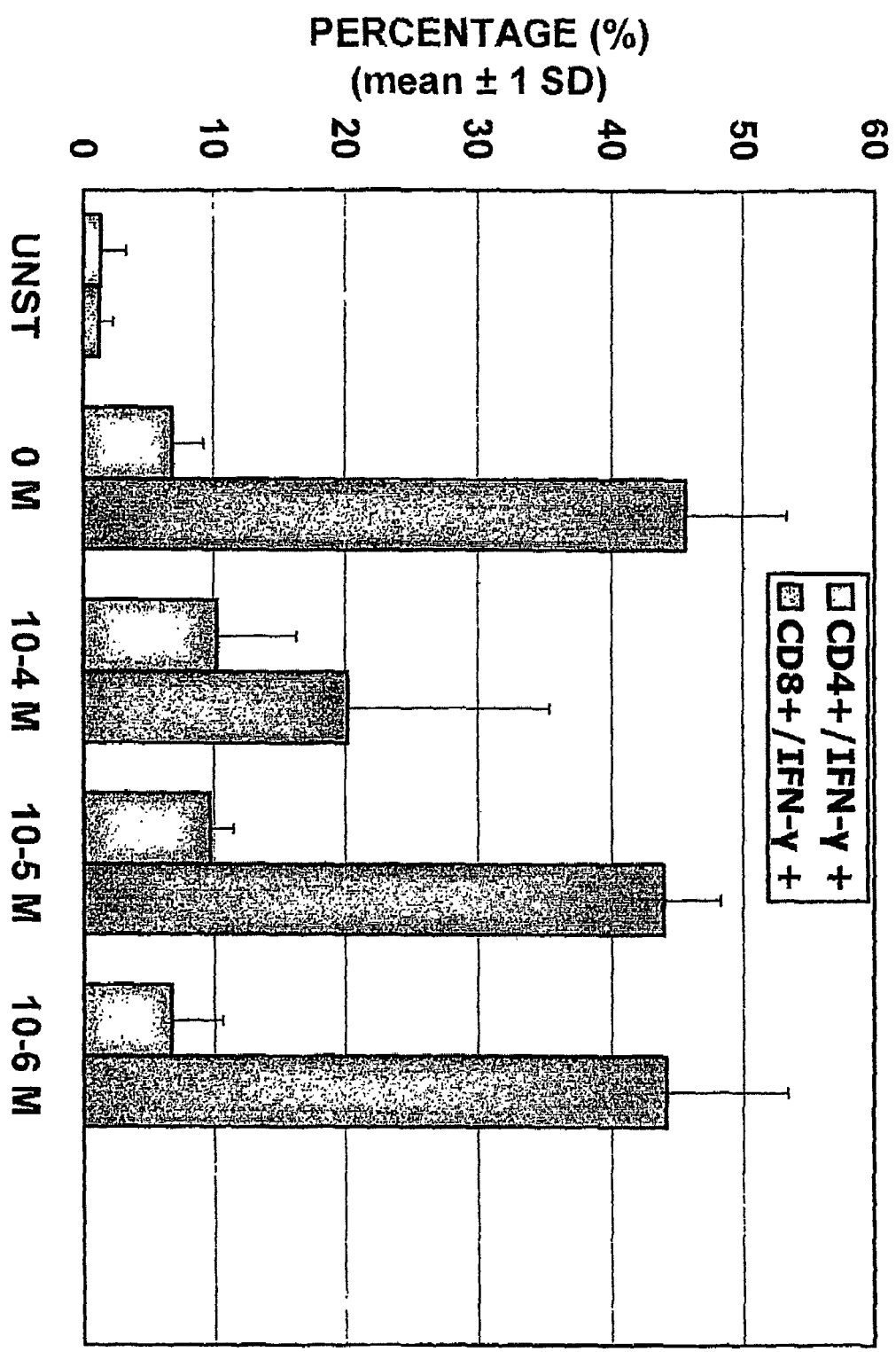
FIG. 11: Effect of $N^1,N^{12}$-$RA_2$-SPM on the percentage of CD8+/IFN-γ+ peripheral blood mononuclear cells.
Figure 12:
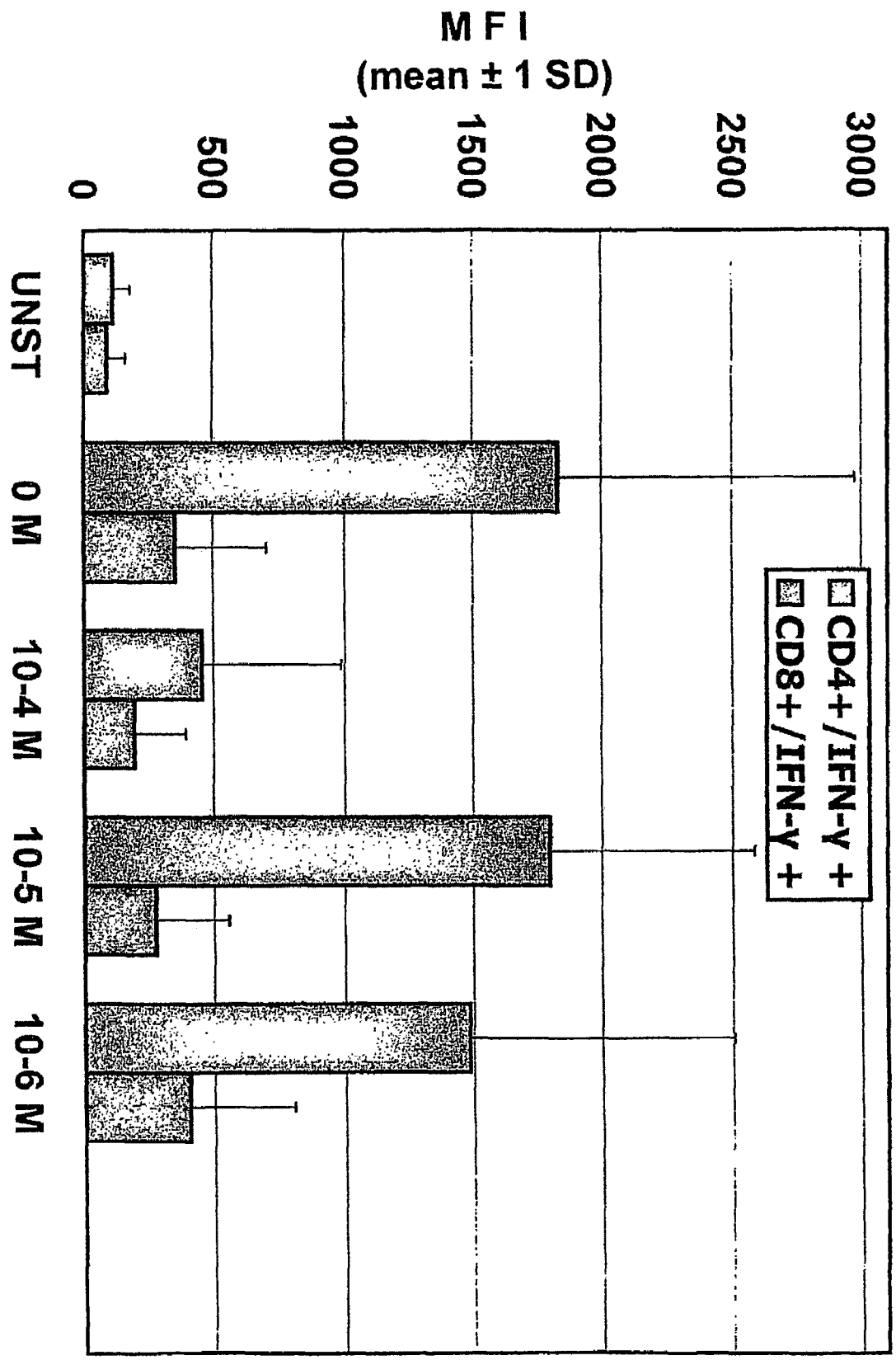
FIG. 12: Effect of $N^1,N^{12}$-$RA_2$-SPM on the mean fluorescence intensity (MFI) of CD8+/IFN-γ+ peripheral blood mononuclear cells.

Following this incubation, PBMC were stained with either an anti-CD4-FITC or anti-CD8-FITC monoclonal antibody (Beckton Dikinson Hellas, Athens, Greece) in a PBS buffer containing 0.5% BSA and 0.01% NaN$_3$, and were subsequently fixed with paraformaldehyde and incubated overnight. In the next step, fixed PBMCs were washed and resuspended in a PBS buffer containing 0.5% BSA, 0.5% saponin (Sigma, St Louis, Mo.) (to permeabilize cells) and 0.01% NaN$_3$. Fixed PBMC were subsequently stained with an anti-IL-2/PE or anti-IFN-γ/PE monoclonal antibody (Diaclone, Besancon, France) and analysed for intracellular expression of IL-2 or IFN-γ and membrane expression of the CD4 or CD8 antigens in a FACSCAN flow cytometer. Throughout this step, saponin-supplied PBS was used, since its permeabilisation effect is reversible. The immunofluorescence cut-off was set up in unstimulated cultures as background and results were expressed either as the percentage of CD4/IL-2+ and CD8/IL-2+ (FIG. 9) and CD8/IFN-γ+ and CD4/IFN-γ+ (FIG. 11) cells, or alternatively as their mean fluorescence intensity (FIGS. 10 and 12, respectively).

It is to be understood that, while the foregoing invention has been described in detail by way of illustration and example, numerous modifications, substitutions and alterations are possible without departing from the spirit and scope of the invention as described in the following claims.

The invention claimed is:

1. One or more conjugate of a polyamine with an acidic retinoid, in which an R group in a) and/or b) below is one of the retinoid residues $R^1$-$R^6$ set forth in the following acidic retinoids, the retinoid residues obtained by removing the COOH group from each of the following acidic retinoids:

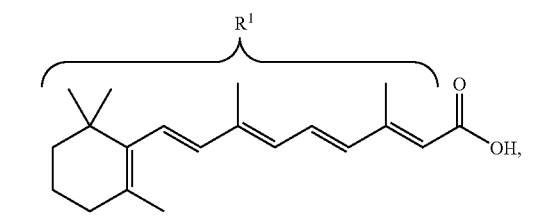

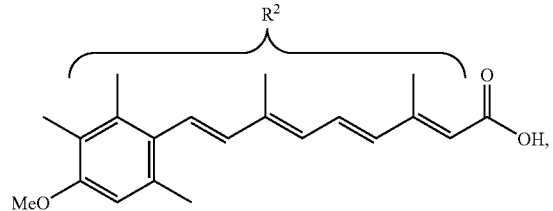

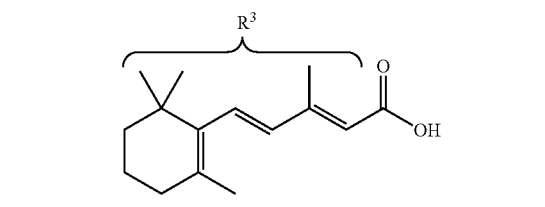

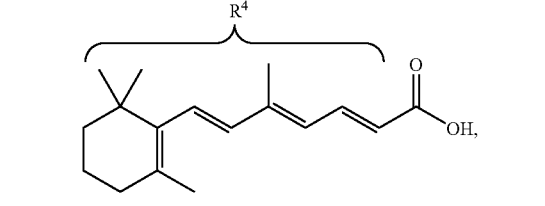

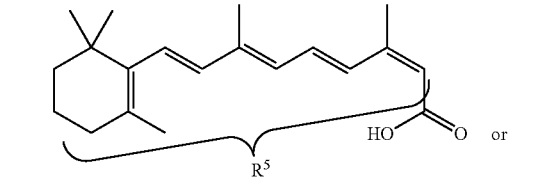

-continued

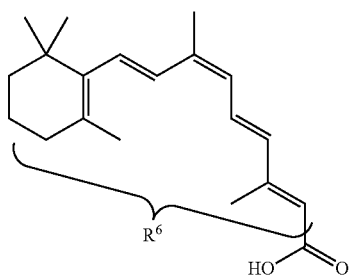

and said polyamine is:

a) a linear polyamine, in which case the one or more conjugate has the following formulae:

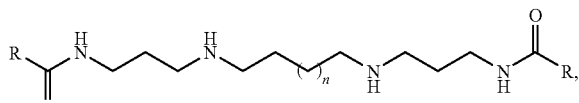

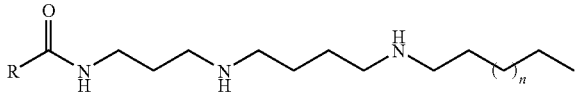

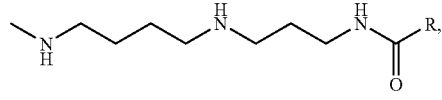

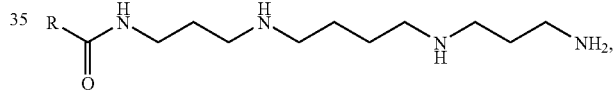

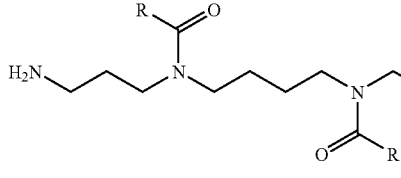

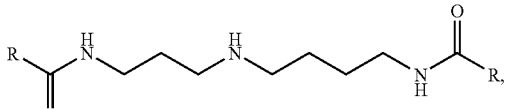

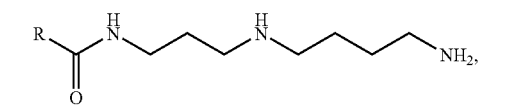

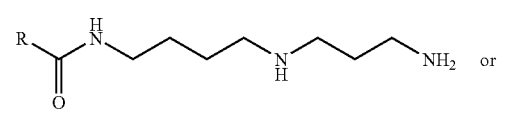

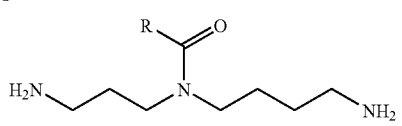

wherein n is 1 to 9; or b) a branched polyamine, in which case the one or more conjugate has the following formula:

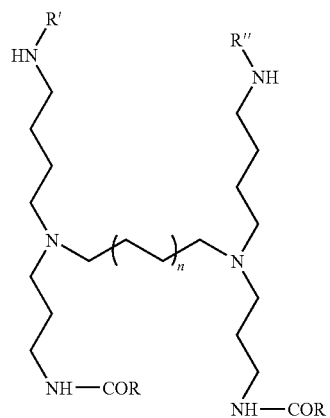

wherein
R' is COR or (CH$_2$)$_3$NHCOR and R'' is COR or (CH$_2$)$_3$NHCOR and n is one of the numbers 1, 2 or 7.

2. A method for the preparation of the one or more conjugate according to claim 1 involving initially step a), followed by step b) or step c):
a) synthesis of a compound with the formula

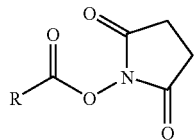

wherein R is one of the retinoid residues R$^1$-R$^6$ of claim 1, which involves esterification of an acidic retinoid with N-hydroxysuccinimide (HOSu) in the presence of a coupling agent, which is N,N'-dicyclohexylcarbodiimide (DCC) and purification with flash column chromatography to obtain a purified succinimidyl ester;
b) direct selective acylation of the primary amino functions of the polyamine with the purified succinimidyl ester; or
c) selective acylation of the secondary amino functions of the polyamine, protected at its primary amino functions with a trifluoroacetyl group or a 9-fluorenylmethoxycarbonyl group, with the acidic retinoid of claim 1 in the presence of a coupling agent, which is bromotripyrrolidinophosphonium hexafluorophosphate (PyBrOP), followed by deprotection.

3. A method according to claim 2, which method involves the direct selective acylation of the primary amino functions of the polyamine or its corresponding hydrochloride or trifluoroacetate salts with the compound of the step a) of claim 2, wherein a solvent is used which is selected from dichloromethane, chloroform and dimethylformamide.

4. A method according to claim 3 wherein the selective acylation of the primary amino functions of the polyamine is carried out with any other activated carboxylic acid derivative known to acylate selectively primary amino functions in the presence of secondary amino functions.

5. A method according to claim 2 wherein selective mono- or bis-acylation of the primary amino functions of the polyamine takes place indirectly and involves the following steps:
(i) protection of the secondary amino functions of the polyamine, bearing the trityl protecting group at its primary amino functions, with the 9-fluorenylmethoxycarbonyl group or the trifluoroacetyl group;
(ii) detritylation;
(iii) mono- or bis-acylation with the compound of step a) of claim 2.

6. A method according to claim 2 wherein the selective acylation of the secondary amino functions of the polyamine involves the following steps:
(i) selective trifluoroacetylation of the primary amino functions of the polyamine;
(ii) acylation of the secondary amino functions with the acidic retinoids in the presence of the coupling agent PyBroP;
(iii) removal of the trifluoroacetyl groups by alkaline hydrolysis.

7. A pharmaceutical preparation or product containing the one or more conjugate claimed in claim 1 and a pharmaceutically acceptable carrier.

8. A method according to claim 3, wherein a base is used which is triethylamine or diisopropylethylamine.

9. A method according to claim 5, which further involves the following step:
(iv) complete deprotection and purification by flash column chromatography.

* * * * *